(12) United States Patent
Arditty et al.

(10) Patent No.: US 9,320,920 B2
(45) Date of Patent: Apr. 26, 2016

(54) WAX-IN-WATER EMULSION COMPRISING A COMBINATION OF A GLUTAMIC ACID DERIVATIVE AND AN ALKYLPOLYGLYCOSIDE

(75) Inventors: Stephane Arditty, Ballainvilliers (FR); Florence Lahousse, Thiais (FR)

(73) Assignee: L'OREAL, Paris (FR)

( * ) Notice: Subject to any disclaimer, the term of this patent is extended or adjusted under 35 U.S.C. 154(b) by 718 days.

(21) Appl. No.: 12/765,481

(22) Filed: Apr. 22, 2010

(65) Prior Publication Data

US 2010/0278770 A1 Nov. 4, 2010

Related U.S. Application Data

(60) Provisional application No. 61/213,172, filed on May 14, 2009.

(30) Foreign Application Priority Data

Apr. 30, 2009 (FR) ..................................... 09 52902

(51) Int. Cl.
| | | |
|---|---|---|
| *A61Q 1/10* | (2006.01) | |
| *A61K 8/06* | (2006.01) | |
| *A61K 8/44* | (2006.01) | |
| *A61K 8/60* | (2006.01) | |
| *A61K 8/34* | (2006.01) | |
| *A61K 8/92* | (2006.01) | |
| *A61Q 1/02* | (2006.01) | |

(52) U.S. Cl.
CPC ... *A61Q 1/10* (2013.01); *A61K 8/06* (2013.01); *A61K 8/44* (2013.01); *A61K 8/604* (2013.01); *A61K 8/922* (2013.01); *A61K 8/927* (2013.01); *A61Q 1/02* (2013.01)

(58) Field of Classification Search
None
See application file for complete search history.

(56) References Cited

U.S. PATENT DOCUMENTS

| | | | |
|---|---|---|---|
| 3,937,811 A | 2/1976 | Papantoniou et al. | |
| 4,578,266 A | 3/1986 | Tietjen et al. | |
| 4,887,622 A | 12/1989 | Gueret | |
| 4,972,037 A | 11/1990 | Garbe et al. | |
| 4,981,902 A | 1/1991 | Mitra et al. | |
| 4,981,903 A | 1/1991 | Garbe et al. | |
| 5,162,410 A | 11/1992 | Sweet | |
| 5,209,924 A | 5/1993 | Garbe et al. | |
| 5,219,560 A | 6/1993 | Suzuki et al. | |
| 5,246,694 A | 9/1993 | Birthwistle | |
| 5,468,477 A | 11/1995 | Kumar et al. | |
| 5,725,882 A | 3/1998 | Kumar et al. | |
| 5,782,580 A * | 7/1998 | Aubert et al. ............ | 405/128.75 |
| 5,874,069 A | 2/1999 | Mendolia et al. | |
| 5,919,441 A | 7/1999 | Mendolia et al. | |
| 5,981,680 A | 11/1999 | Petroff et al. | |
| 5,990,479 A | 11/1999 | Weiss et al. | |
| 6,051,216 A | 4/2000 | Barr et al. | |
| 6,225,198 B1 | 5/2001 | Alivisatos et al. | |
| 6,328,495 B1 | 12/2001 | Gueret | |
| 2004/0120920 A1 | 6/2004 | Lion et al. | |
| 2008/0124292 A1 | 5/2008 | Collin et al. | |
| 2009/0289362 A1 | 11/2009 | Rhyner et al. | |

FOREIGN PATENT DOCUMENTS

| | | |
|---|---|---|
| EP | 0 388 582 A2 | 9/1990 |
| EP | 0 486 135 A2 | 5/1992 |
| EP | 0 773 017 A1 | 5/1997 |
| EP | 773017 A1 * | 5/1997 |
| EP | 0 847 752 A1 | 6/1998 |
| EP | 1 411 069 A2 | 4/2004 |
| EP | 1 920 760 A1 | 5/2008 |
| FR | 2 232 303 | 1/1975 |
| FR | 2 679 771 A1 | 2/1993 |
| FR | 2 761 959 A1 | 10/1998 |
| FR | 2 792 190 A1 | 10/2000 |
| FR | 2 792 618 A1 | 10/2000 |
| FR | 2 796 529 A1 | 1/2001 |
| FR | 2 863 876 A1 | 6/2005 |
| FR | 2863876 A1 * | 6/2005 |
| FR | 2 908 302 A1 | 5/2008 |
| JP | A-5-86984 | 4/1993 |
| JP | A-7-196946 | 8/1995 |
| WO | WO 92/06778 A1 | 4/1992 |
| WO | WO 95/13863 A1 | 5/1995 |
| WO | WO 98/47610 A1 | 10/1998 |
| WO | WO 02/056940 A2 | 7/2002 |
| WO | WO 2004/028488 A2 | 4/2004 |
| WO | WO 2004/055081 A2 | 7/2004 |
| WO | WO 2004/073626 A2 | 9/2004 |

OTHER PUBLICATIONS

Blum et al. Allergic contact dermatitis from mono-, di- and triethanolamine. Contact Dermatitis 1997;36(3)166.*
CAS Registry No. 38517-23-6 (Nov. 16, 1984).*
French Search Report for French Application No. 0952902, Jan. 27, 2010 (w/ English translation).

* cited by examiner

*Primary Examiner* — Bethany Barham
*Assistant Examiner* — Peter Anthopolos
(74) *Attorney, Agent, or Firm* — Oliff PLC

(57) ABSTRACT

The present invention relates to a composition for coating keratin fibers, more particularly the eyelashes, characterized in that it is present in the form of a wax-in-water emulsion comprising a combination of at least one glutamic acid derivative and/or salt thereof and at least one alkylpolyglycoside.

20 Claims, No Drawings

WAX-IN-WATER EMULSION COMPRISING A COMBINATION OF A GLUTAMIC ACID DERIVATIVE AND AN ALKYLPOLYGLYCOSIDE

The present invention provides a cosmetic composition for coating keratin fibres, especially the eyelashes, which takes the form of a wax-in-water emulsion and comprises at least one glutamic acid derivative and/or salt thereof and at least one alkylpolyglycoside.

The composition according to the invention may be a composition for makeup or care of keratin fibres such as the eyelashes, eyebrows and hair. More particularly it is a keratin fibre makeup composition.

More specifically the composition according to the invention is a composition intended for application to the eyelashes, which is also called a "mascara". It may be a makeup composition, a cosmetic basecoat composition or a topcoat composition for application over a cosmetic basecoat composition. The mascara is intended more particularly for the eyelashes of human beings, but also for false eyelashes.

Known mascara formulations include, in particular, emulsion mascaras or washable mascaras, which are composed of a wax or mixture of waxes which are dispersed by means of at least one surfactant in an aqueous phase further comprising polymers which are water-soluble and pigments.

The charging nature of mascaras represented by the thickness of the application on the eyelash, is also a property which is often desired for the purpose of emphasizing the look and making it more intense.

For washable mascaras, the principle for obtaining a volumizing or charging effect involves depositing the maximum amount of material on the eyelashes.

It is more particularly the amount of solid particles, which allow texturing of the composition, that allows the specific required application properties to be set for the compositions, for example their fluidity or consistency, and also their thickening power, also called charging power or makeup power.

These solid particles, and more particularly waxes, are generally dispersed using a surfactant system. The selection of the surfactant system is paramount in the acquisition of a stable dispersion of high consistency, insofar as the surfactants play an important part at the interface in the interactions between wax particles within the formula.

Thus, it is known, for example, that the use of nonionic surfactants alone, not in combination with ionic surfactants, does not produce dispersions of high consistency, and hence does not result in sufficiently charging mascaras. Indeed, since the texture obtained with nonionic surfactants alone is too fluid, the amount of material applied to the eyelashes is low.

Among conventional surfactants or surfactant systems that permit mascaras having a satisfactory charging power to be obtained, there is knowledge in particular of surfactant systems based on triethanolamine stearate, which is used together or not with other surfactants.

However, tertiary, secondary and primary alkanolamines are increasingly less advisable in terms of toxicity.

There remains, therefore, a need to provide cosmetic compositions for coating keratin fibres, especially the eyelashes, which are free of triethanolamine or derivatives thereof and possess a satisfactory charging power, allowing in particular the production of thick makeup on keratin fibres, more particularly the eyelashes, which is also referred to as charging makeup.

A specific object of the present invention is to meet this need.

Document WO 02/056940 relates to foaming compositions containing an emulsifier mixture comprising an acylamino acid, more particularly cocoacyl glutamate, and an alkyl or alkenyl oligoglycoside.

Document EP 0 773 017 teaches cosmetic and pharmaceutical emulsions, especially lotions and creams, which exhibit enhanced stability over time and under high-temperature conditions, comprising the mixture of a $C_{16}$-$C_{22}$ alkylpolyglycoside, a $C_{16}$-$C_{22}$ fatty alcohol and an acylglutamate.

As is apparent from the examples given below, the inventors have found that it is possible to obtain a wax-in-water emulsion which exhibits good charging properties by employing an emulsifier system comprising at least one glutamic acid derivative and/or salt thereof and at least one alkylpolyglycoside.

More specifically, the inventors have observed that a combination of at least one glutamic acid derivative and/or salt thereof and at least one alkylpolyglycoside allows a stable dispersion of a large amount of waxes to be obtained, with the quality of those obtained with emulsifier systems based on triethanolamine stearate.

In the sense of the present invention, the term "keratin fibres" embraces hair, eyelashes and eyebrows, and also extends to artificial hair pieces and false eyelashes.

A "wax-in-water emulsion" for the purposes of the present invention means a composition comprising at least one wax or mixture of waxes dispersed by means of at least one surfactant in a continuous aqueous phase.

"Stable" refers in the sense of the present invention to a composition which, after having been placed in an oven at 45° C. for two months, does not, when returned to ambient temperature, exhibit grains perceptible to the touch when a fine layer of the composition is sheared between the fingers.

Accordingly, the invention relates, in one of its aspects, to a composition for coating keratin fibres, especially eyelashes, which takes the form of a wax-in-water emulsion and comprises a combination of at least one glutamic acid derivative and/or salt thereof and at least one alkylpolyglycoside, said wax or waxes being distinct from fatty alcohols, especially fatty alcohols comprising from 10 to 30 carbon atoms, especially from 12 to 22 carbon atoms.

Advantageously, a composition in accordance with the invention may comprise less than 1%, preferably less than 0.5% by weight of triethanolamine or derivatives thereof, and more preferably may be free of triethanolamine or derivatives thereof.

With particular advantage a composition of the invention may comprise a wax content greater than or equal to 15%, preferably greater than or equal to 18% and more preferably greater than or equal to 20% by weight, relative to the total weight of the composition.

As a result of the high level of waxes it may incorporate, a composition according to the invention thus has a sufficiently thick texture to provide a charging, volumizing application on the eyelashes.

According to one particular embodiment, the compositions according to the invention have viscosities, measured at ambient temperature on a Rheomat 180, of between 2 and 25 Pa·s.

More specifically, the viscosities are measured at 25° C. using a Rheomat 180 (from Lamy) fitted with an MS-R1, MS-R2, MS-R3, MS-R4 or MS-R5 spindle, selected according to the consistency of the composition, which rotates at a speed of 200 rpm. The measurement is taken after 10 minutes of rotation. The viscosity measurements are carried out no later than 1 week after the composition has been prepared.

Viscosity values of this kind convey a high consistency on the part of the compositions according to the invention, which is particularly suited to eyelash makeup, being beneficial more particularly to easy application to the eyelashes and the production of a smooth, homogeneous coating.

According to another of its aspects, the invention relates to a cosmetic process for makeup and/or non-therapeutic care of keratin fibres, especially eyelashes, that comprises applying to said keratin fibres a composition as described above.

The present invention is also directed to the use of a composition as described above for obtaining charging makeup on keratin fibres, more particularly the eyelashes.

In the sense of the present invention, the term "charging" qualifies the idea of thick makeup on the eyelashes.

Glutamic Acid Derivative

The emulsifier system of a composition according to the invention comprises at least one glutamic acid derivative and/or salt thereof.

The salt and/or derivative of glutamic acid may be for example selected from acyl glutamic acids (INCI name: acyl glutamic acid), salts thereof (glutamates) and mixtures thereof, preferably from acyl glutamic acids in which the acyl group comprises from 10 to 30 carbon atoms, preferably from 12 to 22 carbon atoms such as, for example, lauroyl glutamic acid, myristoyl glutamic acid, palmitoyl glutamic acid, stearoyl glutamic acid, behenoyl glutamic acid, olivoyl glutamic acid, cocoyl glutamic acid and the salts with alkali metals such as Na, Li or K, preferably Na or K, the salts with alkaline earth metals such as Mg or the ammonium salts of said acids.

They include in particular the compounds bearing the INCI name lauroyl glutamic acid, cocoyl glutamic acid, sodium stearoyl glutamate, potassium lauroyl glutamate, potassium cocoyl glutamate, sodium olivoyl glutamate, disodium stearoyl glutamate and mixtures thereof.

Compounds of this kind are sold under the name Amisoft by Ajinomoto, and particularly under the references Amisoft CA, Amisoft LA, Amisoft HS 11 PF, Amisoft MK-11, Amisoft LK-11, Amisoft CK-11, or else are sold by Keminova Italiana SRL.

Salts of glutamic acid derivatives further include disodium hydrogenated tallow glutamate such as that sold under the reference Amisoft HS-21 by Ajinomoto.

Likewise included are the commercial mixtures of surfactants comprising at least one glutamic acid derivative or salt of said derivative, such as, for example, a mixture of acyl glutamate salts, such as Amisoft LS-22, sold by Ajinomoto.

According to one particular embodiment, use is made of the monosodium salt of n-stearoyl-L-glutamic acid, more particularly that sold by Ajinomoto under the reference Amisoft HS 11.

The glutamic acid derivative(s) and/or salts thereof may be present in a composition of the invention in an amount of 0.1 to 2% by weight, preferably from 0.2 to 1% by weight, relative to the total weight of the composition.

According to a particular embodiment, the glutamic acid derivative(s) and/or salts thereof are present in the fatty phase or alternatively in the aqueous phase, and advantageously in the aqueous phase of the emulsion.

Alkylpolyglycoside

The emulsifier system of a composition according to the invention comprises at least one alkylpolyglycoside surfactant.

For the purposes of the present invention, an "alkylpolyglycoside" means an alkylmonooside (degree of polymerization: 1) or alkylpolyoside (degree of polymerization: more than 1).

The alkylpolyglycosides may be used alone or in the form of mixtures of two or more alkylpolyglycosides. They conform in general to the following structure:

$R(O)(G)_x$ in which the radical R is a linear or branched $C_{12}$-$C_{22}$ alkyl radical, G is a saccharide residue and x is from 1 to 5, preferably from 1.05 to 2.5 and more preferably from 1.1 to 2.

The saccharide residue may be selected from glucose, dextrose, sucrose, fructose, galactose, maltose, maltotriose, lactose, cellobiose, mannose, ribose, dextran, talose, allose, xylose, levoglucan, cellulose or starch. More preferably the saccharide residue denotes glucose.

It should additionally be noted that each unit of the polysaccharide portion of the alkylpolyglycoside may be in α or β isomeric form, in L or D form, and that the configuration of the saccharide residue may be of furanoside or pyranoside type.

It is of course possible to use mixtures of alkylpolysaccharides, which may differ from one another in the nature of the alkyl moiety borne and/or in the nature of the bearing polysaccharide chain.

According to one particular embodiment of the invention, the alkylpolyglycoside may be used in a mixture with at least one fatty alcohol, especially a fatty alcohol having from 10 to 30 carbon atoms, and more particularly from 12 to 22 carbon atoms, as described later on in the paragraph "Cosurfactants".

Moreover, it is particularly advantageous, according to the present invention, to employ simultaneously a fatty alcohol and an alkylpolyglycoside in which the alkyl portion is identical to that of the fatty alcohol employed.

Fatty alcohol/alkylpolyglycoside emulsifier mixtures as defined above are known per se. They are described especially in patent applications WO 92/06778, WO 95/13863 and WO 98/47610, and are prepared by the preparation processes indicated in these documents.

Particularly preferred fatty alcohol/alkylpolyglycoside mixtures include the products sold by SEPPIC under the Montanov® names, such as the following mixtures:

cetylstearyl alcohol/cocoglucoside—Montanov 82®,
arachidyl alcohol and behenyl alcohol/arachidylglucoside—Montanov 802®,
myristyl alcohol/myristylglucoside—Montanov 14®,
cetylstearyl alcohol/cetylstearylglucoside—Montanov 68®,
$C_{14}$-$C_{22}$ alcohol/$C_{12}$-$C_{20}$ alkylglucoside—Montanov L®,
cocoalcohol/cocoglucoside—Montanov S®, and
isostearyl alcohol/isostearylglucoside—Montanov WO 18®.

According to one particular embodiment, the alkylpolyglycoside employed in a composition according to the invention is cetylstearylglucoside. It is used advantageously in the form of a mixture with cetylstearyl alcohol, which is also called cetearyl alcohol.

According to one particular embodiment of the invention, then, use is made of the cetylstearyl alcohol/cetylstearylglucoside mixture sold by SEPPIC under the name Montanov 68®, composed of about 20% cetylstearylglucoside and about 80% cetylstearyl alcohol.

The fatty alcohol/alkylpolyglycoside mixture may be present in a composition of the invention in an amount of from 1% to 10% by weight and more preferably from 2% to 8% by weight, relative to the total weight of the emulsion.

More particularly, the alkylpolyglycoside surfactant may be present in a composition of the invention in an amount of from 0.2% to 2%, preferably from 0.3% to 1.6% by weight, relative to the total weight of the composition.

According to one particular embodiment, a composition in accordance with the invention may comprise said alkylpolyglycoside and said glutamic acid derivative and/or salt thereof in an alkylpolyglycoside/glutamic acid derivative weight ratio of greater than or equal 0.2, advantageously greater than or equal to 0.3, in particular less than 2, and more particularly less than 1.6.

In the particular case in which the alkylpolyglycoside is employed in combination with at least one fatty alcohol as described above, especially a fatty alcohol having from 10 to 30 carbon atoms, and especially from 12 to 22 carbon atoms, a composition of the invention may then advantageously comprise said mixture of alkylpolyglycoside and fatty alcohol and said glutamic acid derivative and/or salt thereof in an (alkylpolyglycoside+fatty alcohol)/glutamic acid derivative weight ratio of greater than or equal to 2, advantageously greater than or equal to 2.5, in particular less than 10, and more particularly less than 8.

According to one particular embodiment, the emulsifier system of a composition according to the invention comprises a combination of the monosodium salt of n-stearoyl-L-glutamic acid, more particularly that sold by Ajinomoto under the reference Amisoft HS 11, with a cetylstearyl alcohol/cetylstearylglucoside mixture, more particularly that sold by SEPPIC under the name Montanov 68®.

According to one particular embodiment, the combination according to the invention of a glutamic acid derivative and/or salt thereof and an alkylpolyglycoside may constitute the principal surfactant system of the composition.

By "principal surfactant system" is meant a system which, in its absence, does not result in the formation of a stable composition.

According to one particular embodiment, the combination according to the invention, of glutamic acid derivative and/or salt thereof/alkylpolyglycoside, may constitute the sole surfactant system of the composition.

By "sole" is meant that any additional surfactant system is present in an amount not exceeding 1%, and preferably not exceeding 0.5%. More preferably, "sole" denotes total absence of any other surfactant system.

The compositions according to the invention comprise, of course, a medium which is physiologically acceptable, in other words compatible with application to keratin materials, more particularly the eyelashes.

Aqueous Phase

The composition according to the invention comprises an aqueous phase, which forms the continuous phase of the wax-in-water emulsion of the invention.

By "composition with aqueous continuous phase" is meant that the composition has a conductivity, measured at 25° C., of greater than or equal to 23 µS/cm (microsiemens/cm), the conductivity being measured, for example, using a Mettler Toledo MPC227 conductimeter and an Inlab730 conductivity measuring cell. The measuring cell is immersed in the composition, in such a way as to remove the bubbles of air that may be formed between the 2 electrodes of the cell. The conductivity is read off when the value on the conductimeter is stabilized. An average is carried out on at least 3 successive measurements.

The aqueous phase comprises water and/or at least one water-soluble solvent.

By "water-soluble solvent" is meant, in the present invention, a compound which is liquid at ambient temperature and is miscible with water (miscibility in water greater than 50% by weight at 25° C. and atmospheric pressure).

The water-soluble solvents which can be used in the compositions according to the invention may additionally be volatile.

Water-soluble solvents which may be used in the compositions in accordance with the invention include, especially, lower monoalcohols having from 1 to 5 carbon atoms, such as ethanol and isopropanol, glycols having from 2 to 8 carbon atoms, such as ethylene glycol, propylene glycol, 1,3-butylene glycol and dipropylene glycol, $C_3$-$C_4$ ketones and $C_2$-$C_4$ aldehydes.

The aqueous phase (water and, where appropriate, water-miscible solvent) is generally present in the composition according to the present application in an amount of from 30% to 95% by weight, relative to the total weight of the composition, preferably from 40% to 80% by weight and more preferably from 45% to 60% by weight.

Waxes

The compositions according to the invention comprise, generally, a wax or a mixture of waxes, in the form of an aqueous dispersion of wax particles.

As specified above, a wax-in-water emulsion according to the invention may comprise at least 15% by weight of waxes, preferably at least 18% by weight and more preferably at least 20% by weight of waxes, relative to the total weight of the composition.

The wax in question in the context of the present invention is, in general, a lipophilic compound which is solid at ambient temperature (25° C.), exhibits a reversible solid/liquid state change, has a melting point of greater than or equal to 30° C. and possibly up to 120° C., with the exception of fatty alcohols as described below, especially fatty alcohols having from 10 to 30 carbon atoms and especially from 12 to 22 carbon atoms.

By taking the wax into the liquid state (melting), it is possible to make it miscible with the oils and to form a microscopically homogeneous mixture; however, by lowering the temperature of the mixture to ambient temperature, there is recrystallization of the wax in the oils of the mixture.

More particularly, waxes suitable for the invention may have a melting point of greater than about 45° C., and more particularly greater than 55° C.

The melting point of the wax may be measured using a differential scanning calorimeter (DSC), an example being the calorimeter sold by Mettler under the name DSC 30.

The measurement protocol is as follows:

A 15 mg sample of product in a crucible is subjected to a first temperature rise from 0° C. to 120° C., at a heating rate of 10° C./minute, and is cooled from 120° C. to 0° C. at a cooling rate of 10° C./minute, and finally is subjected to a second temperature rise from 0° C. to 120° C. at a heating rate of 5° C./minute. During the second temperature rise, the variation in the power difference absorbed by the empty crucible and by the crucible containing the sample of product is measured as a function of the temperature. The melting point of the compound is the temperature value corresponding to the top of the peak of the curve representing the variation in the difference in power absorbed as a function of the temperature.

The waxes which can be used in the compositions according to the invention are selected from solid waxes which are deformable or non-deformable at ambient temperature and are of animal, plant, mineral or synthetic origin, and mixtures thereof.

The wax may also have a hardness of from 0.05 MPa to 30 MPa, and preferably from 6 MPa to 15 MPa. The hardness is determined by measuring the compression force measured at 20° C. with the aid of the texturometer sold under the name TA-TX2i by Rheo, equipped with a stainless steel cylinder with a diameter of 2 mm which moves at a measuring speed of 0.1 mm/s and penetrates the wax to a depth of 0.3 mm.

The measurement protocol is as follows:

The wax is melted at a temperature equal to the melting point of the wax+20° C. The melted wax is poured into a container with a diameter of 30 mm and a depth of 20 mm. The wax is recrystallized at ambient temperature (25° C.) for 24 hours and then the wax is kept at 20° C. for at least 1 hour before the hardness measurement is performed. The value of the hardness is the maximum compression force measured, divided by the surface area of the cylinder of the texturometer that is in contact with the wax.

Use may be made in particular of hydrocarbon waxes such as beeswax, lanolin wax and Chinese insect waxes; rice wax, carnauba wax, candelilla wax, ouricury wax, alfa wax, cork fibre wax, sugarcane wax, Japan wax and sumac wax; montan wax, microcrystalline waxes, paraffins and ozokerite; polyethylene waxes, waxes obtained by Fischer-Tropsch synthesis, and waxy copolymers, and also their esters.

Mention may also be made of the waxes obtained by catalytic hydrogenation of animal or vegetable oils having $C_8$-$C_{32}$ linear or branched fatty chains.

Among these, mention may be made more particularly of hydrogenated jojoba oil, hydrogenated sunflower oil, hydrogenated castor oil, hydrogenated copra oil and hydrogenated lanolin oil, the di(1,1,1-trimethylolpropane) tetrastearate sold under the name Hest 2T-4S by Heterene and the di(1,1,1-trimethylolpropane) tetrabehenate sold under the name Hest 2T-4B by Heterene.

It is also possible to use the waxes obtained by transesterification and hydrogenation of vegetable oils, such as castor oil or olive oil, such as the waxes sold under the names Phytowax ricin 16L64® and 22L73® and Phytowax Olive 18L57 by Sophim. Waxes of this kind are described in Patent Application FR-A-2792190.

It is also possible to use silicone waxes, which may advantageously be substituted polysiloxanes, preferably having a low melting point. These are, more particularly, substituted linear polysiloxanes composed essentially (with the exception of the end groups) of units of formulae II and III, in the respective molar proportions in and n:

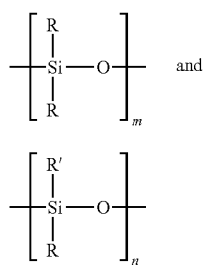

in which
each substituent R is defined as above,
each R' independently represents an optionally unsaturated (linear or branched) alkyl having 6-30 carbon atoms, or else a group —X—R", each X independently representing:
—O—,

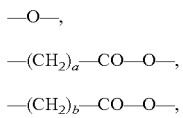

a and b independently representing numbers from 0 to 6, and each R" independently represents an optionally unsaturated alkyl group having 6 to 30 carbon atoms, m is a number from 0 to 400, and in particular from 0 to 100, n is a number from 1 to 200, and in particular from 1 to 100, the sum (m+n) being less than 400, and in particular less than or equal to 100.

These silicone waxes are known or can be prepared in accordance with known processes. The commercial silicone waxes of this type include, more particularly, those sold under the names Abilwax 9800, 9801 or 9810 (Goldschmidt), KF910 and KF7002 (Shin Etsu), or 176-1118-3 and 176-11481 (General Electric).

The silicone waxes which can be used may also be selected from the compounds of formula (IV) below:

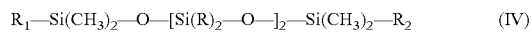

in which:
R is defined as above,
$R_1$ represents an alkyl group having 1 to 30 carbon atoms, an alkoxy group having 6 to 30 carbon atoms, or a group of formula:

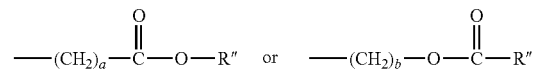

$R_2$ represents an alkyl group of 6 to 30 carbon atoms, an alkoxy group having 6 to 30 carbon atoms or a group of formula:

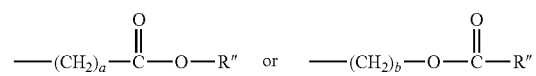

a and b representing a number from 0 to 6,
R" being an alkyl having from 6 to 30 carbon atoms,
and z is a number from 1 to 100.

The silicone waxes of formula (IV) include more particularly the alkyldimethicones or alkoxydimethicones such as the following commercial products: Abilwax 2428, 2434 and 2440 (Goldschmidt), or VP 1622 and VP 1621 (Wacker), and also ($C_{20}$-$C_{60}$)alkyldimethicones, in particular ($C_{30}$-$C_{45}$) alkyldimethicones, such as the silicone wax sold under the name SF-1642 by GE-Bayer Silicones.

It is also possible to use hydrocarbon waxes which are modified with silicone or fluoro groups, such as, for example, the following: siliconyl candelilla, siliconyl beeswax and Fluorobeeswax from Koster Keunen.

The waxes may also be selected from fluorowaxes.

According to one particular embodiment the compositions according to the invention may comprise at least one wax referred to as a tacky wax and hence possessing a tack of greater than or equal to 0.7 N·s and a hardness of less than or equal to 3.5 MPa.

The use of a tacky wax may in particular allow a cosmetic composition to be obtained which applies easily to the eyelashes, has good adhesion to the eyelashes, and leads to the formation of a smooth, homogeneous and thickening makeup.

The tacky wax used may more particularly possess a tack of from 0.7 N·s to 30 N·s, in particular greater than or equal to 1 N·s, more particularly from 1 N·s to 20 N·s, in particular greater than or equal to 2 N·s, more particularly from 2 N·s to 10 N·s, and in particular from 2 N·s to 5 N·s.

The tack of the wax is determined by measuring the change in force (compression force or drawing force) as a function of time, at 20° C., using the texturometer sold under the name TA-TX2i® by Rheo, equipped with a conical acrylic polymer spindle forming an angle of 45°.

The measurement protocol is as follows:

The wax is melted at a temperature equal to the melting point of the wax+10° C. The melted wax is poured into a container with a diameter of 25 mm and a depth of 20 mm. The wax is recrystallized at ambient temperature (25° C.) for 24 hours such that the surface of the wax is flat and smooth, and then the wax is kept at 20° C. for at least 1 hour before the tack is measured.

The texturometer spindle is moved at a speed of 0.5 mm/s and then penetrates the wax to a depth of 2 mm. When the spindle has penetrated the wax to the depth of 2 mm, the spindle is held still for 1 second (corresponding to the relaxation time) and then is withdrawn at a speed of 0.5 mm/s.

During the relaxation time, the force (compression force) decreases greatly until it becomes zero, and then, when the spindle is withdrawn, the force (drawing force) becomes negative and then rises again to the value 0. The tack corresponds to the integral of the curve of the force as a function of time for the part of the curve that corresponds to negative values of the force (drawing force). The tack value is expressed in N·s.

The tacky wax which can be used has generally a hardness of less than or equal to 3.5 MPa, in particular from 0.01 MPa to 3.5 MPa, more particularly from 0.05 MPa to 3 MPa, and even from 0.1 MPa to 2.5 MPa.

The hardness is measured according to the protocol described above.

As a tacky wax it is possible to use a $C_{20}$-$C_{40}$ alkyl (hydroxystearyloxy)stearate (the alkyl group containing 20 to 40 carbon atoms), alone or in a mixture, in particular a $C_{20}$-$C_{40}$ alkyl 12-(12'-hydroxystearyloxy)stearate.

A wax of this kind is sold more particularly under the names Kester Wax K 82 P® and Kester Wax K 80 P® by Koster Keunen.

The aforementioned waxes generally have a melting point commencing at below 45° C.

The wax or waxes may be present in the form of an aqueous wax microdispersion. An "aqueous wax microdispersion" is an aqueous dispersion of wax particles in which the size, expressed as the volume-average "effective" diameter D[4,3], of said wax particles is less than or equal to approximately 1 μm.

The wax microdispersions are stable dispersions of colloidal wax particles and are described more particularly in "Microemulsions Theory and Practice", L. M. Prince Ed., Academic Press (1977) pages 21-32.

In particular these wax microdispersions may be obtained by melting the wax in the presence of a surfactant, and optionally part of the water, and then progressively adding hot water with stirring. The intermediate formation of a water-in-oil emulsion is observed, followed by a phase inversion, leading finally to an oil-in-water microemulsion being obtained. On cooling, a stable microdispersion of solid colloidal wax particles is obtained.

The wax microdispersions may also be obtained by stirring the mixture of wax, surfactant and water using stirrer means such as ultrasound, a high-pressure homogenizer or turbines.

The particles of the wax microdispersion preferably have average dimensions of less than 1 μm (more particularly from 0.02 μm to 0.99 μm), preferably less than 0.5 μm (more particularly from 0.06 μm to 0.5 μm).

These particles are composed essentially of a wax or of a mixture of waxes. They may, however, comprise, to a minor extent, oily and/or pasty fatty additives, a surfactant and/or a customary fat-soluble additive/active.

Pasty Compounds

The composition according to the invention may further comprise at least one pasty compound.

A "pasty compound" in the sense of the present invention refers to a lipophilic fatty compound which exhibits a reversible solid/liquid state change and which, at a temperature of 23° C., comprises a liquid fraction and a solid fraction.

In other words, the starting melting point of the pasty compound is less than 23° C. The liquid fraction of the pasty compound measured at 23° C. represents from 20% to 97% by weight of the pasty compound. This fraction that is liquid at 23° C. more preferentially represents from 25% to 85% and better still from 30% to 60% by weight of the pasty compound.

The liquid fraction by weight of the pasty compound at 23° C. is equal to the ratio of the enthalpy of fusion consumed at 23° C. to the enthalpy of fusion of the pasty compound.

The enthalpy of fusion consumed at 23° C. is the amount of energy absorbed by the sample to change from the solid state to the state that it has at 23° C., composed of a liquid fraction and a solid fraction.

The enthalpy of fusion of the pasty compound is the enthalpy consumed by the compound to change from the solid state to the liquid state. The pasty compound is said to be in the solid state when all of its mass is in solid form. The pasty compound is said to be in the liquid state when all of its mass is in liquid form.

The enthalpy of fusion of the pasty compound is equal to the area under the curve of the thermogram obtained using a differential scanning calorimeter (DSC), such as the calorimeter sold under the name MDSC 2920 by the company TA Instrument, with a temperature rise of 5 or 10° C. per minute, according to standard ISO 11357-3:1999. The enthalpy of fusion of the pasty compound is the amount of energy required to make the compound change from the solid state to the liquid state. It is expressed in Jig.

The liquid fraction of the pasty compound, measured at 32° C., preferably represents from 40% to 100% by weight of the pasty compound and better still from 50% to 100% by weight of the pasty compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same manner as the enthalpy of fusion consumed at 23° C.

The pasty compound preferably has a hardness at 20° C. ranging from 0.001 to 0.5 MPa and preferably from 0.002 to 0.4 MPa.

The hardness is measured according to a method of penetration of a probe into a sample of compound and in particular using a texture analyzer (for example the TA-XT2i from Rhéo) equipped with a stainless-steel cylinder 2 mm in diameter. The hardness measurement is performed at 20° C. at the centre of five samples. The cylinder is introduced into each sample, the penetration depth being 0.3 mm. The hardness value recorded is that of the maximum peak.

The pasty compound may be selected from synthetic compounds and compounds of plant origin. A pasty compound may be obtained by synthesis from starting materials of plant origin.

The pasty compound is advantageously selected from:
lanolin and derivatives thereof such as lanolin alcohol, oxyethylenated lanolins, acetylated lanolin, lanolin esters such as isopropyl lanolate, and oxypropylenated lanolins,
polymeric or non-polymeric silicone compounds, for instance polydimethylsiloxanes of high molecular masses, and polydimethylsiloxanes with side chains of the alkyl or alkoxy type containing from 8 to 24 carbon atoms, especially stearyl dimethicones,
polymeric or non-polymeric fluoro compounds,
vinyl polymers, especially:
olefin homopolymers
olefin copolymers
hydrogenated diene homopolymers and copolymers
linear or branched oligomers which are homopolymers or copolymers of alkyl (meth)acrylates preferably containing a $C_8$-$C_{30}$ alkyl group
oligomers which are homopolymers and copolymers of vinyl esters containing $C_8$-$C_{30}$ alkyl groups
oligomers which are homopolymers and copolymers of vinyl ethers containing $C_8$-$C_{30}$ alkyl groups,
lipid-soluble polyethers resulting from the polyetherification between one or more $C_2$-$C_{100}$ and preferably $C_2$-$C_{50}$ diols,
esters and polyesters,
and mixtures thereof.

The pasty compound may be a polymer and especially a hydrocarbon-based polymer.

A preferred silicone and fluoro pasty compound is polymethyl trifluoropropyl methylalkyl dimethylsiloxane, manufactured under the name X22-1088 by Shin-Etsu.

When the pasty compound is a silicone and/or fluoro polymer, the composition advantageously comprises a compatibilizer such as short-chain esters, for instance isodecyl neopentanoate.

Among the lipid-soluble polyethers that may especially be mentioned are copolymers of ethylene oxide and/or of propylene oxide with $C_6$-$C_{30}$ alkylene oxides. Preferably, the weight ratio of the ethylene oxide and/or of the propylene oxide to the alkylene oxides in the copolymer is from 5:95 to 70:30. In this family, mention will be made especially of block copolymers comprising $C_6$-$C_{30}$ alkylene oxide blocks with a molecular weight of from 1000 to 10 000, for example a polyoxyethylene/polydodecylene glycol block copolymer such as the ethers of dodecanediol (22 mol) and of polyethylene glycol (45 oxyethylene or OE units) sold under the brand name Elfacos ST9 by Akzo Nobel.

Among the esters that are especially preferred are:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, isostearic acid and 12-hydroxystearic acid, for instance those sold under the brand name Softisan 649 by the company Sasol,
phytosterol esters,
pentaerythritol esters,
esters formed from:
at least one $C_{16-40}$ alcohol, at least one of the alcohols being a Guerbet alcohol, and
a diacid dimer formed from at least one unsaturated $C_{18-40}$ fatty acid,
for instance the ester of fatty acid dimer of tall oil containing 36 carbon atoms and of a mixture i) of Guerbet alcohols containing 32 carbon atoms and ii) of behenyl alcohol; the ester of linoleic acid dimer and of a mixture of two Guerbet alcohols, 2-tetradecyl-octadecanol (32 carbon atoms) and 2-hexadecyleicosanol (36 carbon atoms),
non-crosslinked polyesters resulting from polycondensation between a linear or branched $C_4$-$C_{50}$ dicarboxylic acid or polycarboxylic acid and a $C_2$-$C_{50}$ diol or polyol,
polyesters resulting from esterification between a polycarboxylic acid and an aliphatic hydroxycarboxylic acid ester, for instance Risocast DA-L and Risocast DA-H sold by the Japanese company Kokyu Alcohol Kogyo, which are esters resulting from the esterification reaction of hydrogenated castor oil with dilinoleic acid or isostearic acid, and
aliphatic esters of an ester resulting from esterification between and an aliphatic hydroxycarboxylic acid ester and an aliphatic carboxylic acid, for example the product sold under the trade name Salacos HCIS (V)-L sold by the company Nishing Oil.

A Guerbet alcohol is the reaction product of the Guerbet reaction, which is well known to those skilled in the art. This is a reaction that transforms a primary aliphatic alcohol into its β-alkyl dimer alcohol with loss of one equivalent of water.

The aliphatic carboxylic acids described above generally contain from 4 to 30 and preferably from 8 to 30 carbon atoms. They are preferably selected from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof.

The aliphatic carboxylic acids are preferably branched.

The aliphatic hydroxycarboxylic acid esters are advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid esters are especially selected from:
a) partial or total esters of saturated linear monohydroxylated aliphatic monocarboxylic acids;
b) partial or total esters of unsaturated monohydroxylated aliphatic monocarboxylic acids;
c) partial or total esters of saturated monohydroxylated aliphatic polycarboxylic acids;
d) partial or total esters of saturated polyhydroxylated aliphatic polycarboxylic acids;
e) partial or total esters of $C_2$ to $C_{16}$ aliphatic polyols that have reacted with a monohydroxylated or polyhydroxylated aliphatic monocarboxylic or polycarboxylic acid,
f) and mixtures thereof.

The aliphatic esters of an ester are advantageously selected from:
the ester resulting from the esterification reaction of hydrogenated castor oil with isostearic acid in proportions of 1 to 1 (1/1), known as hydrogenated castor oil monoisostearate,
the ester resulting from the esterification reaction of hydrogenated castor oil with isostearic acid in proportions of 1 to 2 (1/2), known as hydrogenated castor oil diisostearate, the ester resulting from the esterification reaction of hydrogenated castor oil with isostearic acid in proportions of 1 to 3 (1/3), known as hydrogenated castor oil triisostearate, and mixtures thereof.

Preferably, the pasty compound is selected from compounds of plant origin.

Among these compounds, mention may be made especially of isomerized jojoba oil such as the trans-isomerized partially hydrogenated jojoba oil manufactured or sold by the company Desert Whale under the commercial reference Iso-Jojoba-50®, orange wax, for instance the product sold under the reference Orange Peel Wax by the company Koster Keunen, cupuacu butter (Rain forest RF3410), murumuru butter (murumuru butter from the company Beraca Sabara), shea butter, partially hydrogenated olive oil, for instance the compound sold under the reference Beurrolive by the company Soliance, cocoa butter, and mango oil, for instance Lipex 302 from the company Aarhuskarlshamn.

According to one particular embodiment a composition according to the invention comprises shea butter.

The pasty compound or compounds are present preferably in a greater amount of from 0.5% to 10% by weight, especially from 0.5% to 6% by weight, relative to the total weight of the composition.

Additional Surfactants and Cosurfactants

The composition according to the invention may, besides the combination of surfactants according to the invention, comprise at least one additional surfactant and/or at least one cosurfactant, more particularly selected in an appropriate way for obtaining a wax-in-water emulsion.

The additional surfactants may be selected from anionic, nonionic, cationic, amphoteric or zwitterionic surfactants. Reference may be made to Encyclopedia of Chemical Technology, Kirk-Othmer, volume 22, pp. 333-432, 3rd edition, 1979, Wiley, for the definition of the properties and functions (emulsifying) of the surfactants, more particularly pp. 347-377 of said reference, for the anionic and nonionic surfactants.

The additional surfactants may be selected from:

a) nonionic surfactants with an HLB of greater than or equal to 8 at 25° C., used alone or as a mixture; mention may be made especially of:

oxyethylenated and/or oxypropylenated ethers (which may comprise from 1 to 150 oxyethylene and/or oxypropylene groups) of glycerol;

oxyethylenated and/or oxypropylenated ethers (which may comprise from 1 to 150 oxyethylene and/or oxypropylene groups) of fatty alcohols (especially of $C_8$-$C_{24}$ and preferably $C_{12}$-$C_{18}$ alcohol), such as oxyethylenated stearyl alcohol ether containing 20 oxyethylene groups (CTFA name steareth-20) such as BRIJ 78 sold by Uniqema and the oxyethylenated cetearyl alcohol ether containing 30 oxyethylene groups (CTFA name Ceteareth-30) and the oxyethylenated ether of the mixture of $C_{12}$-$C_{15}$ fatty alcohols comprising 7 oxyethylene groups (CTFA name $C_{12-15}$ Pareth-7 sold under the name Neodol 25-7® by Shell Chemicals);

fatty acid esters (especially of a $C_8$-$C_{24}$ and preferably $C_{16}$-$C_{22}$ acid) of polyethylene glycol (which may comprise from 1 to 150 ethylene glycol units), such as PEG-50 stearate and PEG-40 monostearate sold under the name Myrj 52P by the company ICI Uniqema;

fatty acid esters (especially of a $C_8$-$C_{24}$ and preferably $C_{16}$-$C_{22}$ acid) of oxyethylenated and/or oxypropylenated glycerol ethers (which may comprise from 1 to 150 oxyethylene and/or oxypropylene groups), for instance PEG-200 glyceryl monostearate sold under the name Simulsol 220™ by the company SEPPIC; glyceryl stearate polyethoxylated with 30 ethylene oxide groups, for instance the product Tagat S sold by the company Goldschmidt, glyceryl oleate polyethoxylated with 30 ethylene oxide groups, for instance the product Tagat O sold by the company Goldschmidt, glyceryl cocoate polyethoxylated with 30 ethylene oxide groups, for instance the product Varionic LI 13 sold by the company Sherex, glyceryl isostearate polyethoxylated with 30 ethylene oxide groups, for instance the product Tagat L sold by the company Goldschmidt, and glyceryl laurate polyethoxylated with 30 ethylene oxide groups, for instance the product Tagat I from the company Goldschmidt;

fatty acid esters (especially of a $C_8$-$C_{24}$ and preferably $C_{16}$-$C_{22}$ acid) of oxyethylenated and/or oxypropylenated sorbitol ethers (which may comprise from 1 to 150 oxyethylene and/or oxypropylene groups), for instance polysorbate 60 sold under the name Tween 60 by the company Uniqema;

dimethicone copolyol, such as the product sold under the name Q2-5220 by the company Dow Corning;

dimethicone copolyol benzoate (Finsolv SLB 101 and 201 from the company Fintex);

copolymers of propylene oxide and of ethylene oxide, also known as EO/PO polycondensates, for instance the polyethylene glycol/polypropylene glycol/polyethylene glycol triblock polycondensates sold under the name Synperonic, for instance Synperonic PE/L44 and Synperonic PE/F127, by the company ICI;

and mixtures thereof.

b) nonionic surfactants with an HLB of less than 8 at 25° C., optionally combined with one or more nonionic surfactants with an HLB of greater than 8 at 25° C., such as:

saccharide esters and ethers, such as sucrose stearate, sucrose cocoate and sorbitan stearate, and mixtures thereof, for instance Arlatone 2121 sold by the company ICI;

fatty acid esters (especially of a $C_8$-$C_{24}$ and preferably $C_{16}$-$C_{22}$ acid) of polyols, especially of glycerol or of sorbitol, such as glyceryl stearate, such as the product sold under the name Tegin M by the company Goldschmidt, glyceryl laurate, such as the product sold under the name Imwitor 312 by the company Hills, polyglyceryl-2 stearate, sorbitan tristearate or glyceryl ricinoleate;

Oxyethylenated and/or oxypropylenated ethers, such as the oxyethylenated stearyl alcohol ether containing 2 ethylene oxide units (CTFA name Steareth-2), for instance Brij 72 sold by the company Uniqema;

the mixture of cyclomethicone/dimethicone copolyol sold under the name Q2-3225C by the company Dow Corning.

c) anionic surfactants such as:

$C_{16}$-$C_{30}$ fatty acid salts, especially those derived from amines, for instance triethanolamine stearate and/or 2-amino-2-methylpropane-1,3-diol stearate; preferably, however, the composition according to the present patent application comprises less than 1% of triethanolamine stearate;

polyoxyethylenated fatty acid salts, especially those derived from amines or alkali metal salts, and mixtures thereof;

phosphoric esters and salts thereof, such as DEA oleth-10 phosphate (Crodafos N 10N from the company Croda) and cetyl phosphate (Amphisol K from the company DSM Nutritional Products);

sulphosuccinates such as Disodium PEG-5 citrate lauryl sulphosuccinate and Disodium ricinoleamido MEA sulphosuccinate;

alkyl ether sulphates, such as sodium lauryl ether sulphate; isethionates;

acylglutamates such as Disodium hydrogenated tallow glutamate (Amisoft HS-21 R sold by the company Ajinomoto), and mixtures thereof.

The composition in accordance with the invention may also comprise, besides the glutamic acid derivative, one or more amphoteric surfactants, for instance N-acylamino acids such as N-alkylaminoacetates and disodium cocoamphodiacetate and amine oxides such as stearamine oxide, or else silicone surfactants, for instance dimethicone copolyol phosphates, such as that sold under the name Pecosil PS 100® by the company Phoenix Chemical.

According to one particular embodiment the additional surfactant may be glyceryl monostearate and/or distearate.

According to one preferred embodiment a composition in accordance with the invention comprises less than 1%, preferably less than 0.5%, by weight of triethanolamine or derivatives thereof, and more preferably is free of triethanolamine or derivatives thereof.

The cosurfactants may especially be selected from fatty alcohols comprising preferably from 10 to 30 carbon atoms. A fatty alcohol comprising from 10 to 30 carbon atoms is any pure, saturated or unsaturated, branched or unbranched alcohol that comprises from 10 to 30 carbon atoms.

Examples of fatty alcohols which can be used in combination with the alkylpolyglycoside(s) of the emulsifier system according to the invention include linear or branched fatty alcohols of synthetic origin or else of natural origin, such as, for example, the alcohols originating from plant substances (coconut, palm kernel, palm, etc.) or animal substances (tallow, etc.). Of course, other long-chain alcohols may also be used, for example ether alcohols or else what are known as Guerbet alcohols. Finally, it is also possible to use certain longer or shorter fractions of alcohols of natural origin, for example coco ($C_{12}$ to $C_{16}$) or tallow ($C_{16}$ to $C_{18}$) or diol compounds or cholesterol.

It is preferred to use a fatty alcohol comprising from 10 to 26 carbon atoms, preferably from 10 to 24 carbon atoms and more preferably from 12 to 22 carbon atoms.

Particular examples of fatty alcohols which can be used in the context of the present invention include, in particular, lauryl alcohol, myristyl alcohol, cetyl alcohol, stearyl alcohol, isostearyl alcohol, palmityl alcohol, oleyl alcohol, cetearyl alcohol (a mixture of cetyl alcohol and stearyl alcohol), behenyl alcohol, erucyl alcohol, arachidyl alcohol and mixtures thereof. Preference is given to using cetearyl alcohol.

Fatty alcohols of these kinds are especially sold under the name Nafol by the company Sasol.

As described above, these fatty alcohols may be employed together with the alkylpolyglycoside(s) according to the invention, in commercially available fatty alcohol/alkylpolyglycoside mixtures, such as, for example, the cetylstearyl alcohol and cetylstearylglucoside mixture sold by the company SEPPIC under the reference Montanov 68®.

The cosurfactant or cosurfactants may be present in an amount of from 0.1% to 10% by weight, preferably from 0.5% to 8% by weight and more preferably from 1% to 6% by weight, relative to the total weight of the composition.

The overall surfactant content of a composition of the invention may be from 0.5% to 15% by weight, relative to the total weight of the composition, preferably from 1% to 10% by weight.

Film-Forming Polymer

A composition according to the present invention may further comprise at least one film-forming polymer.

Among the film-forming polymers that may be used in the compositions of the present invention, mention may be made of synthetic polymers, of free-radical type or of polycondensate type, and polymers of natural origin, and mixtures thereof.

The expression "free-radical film-forming polymer" means a polymer obtained by polymerization of unsaturated and especially ethylenically unsaturated monomers, each monomer being capable of homopolymerizing (unlike polycondensates).

The film-forming polymers of free-radical type may be, in particular, vinyl polymers or copolymers, in particular acrylic polymers.

The vinyl film-forming polymers may result from the polymerization of ethylenically unsaturated monomers containing at least one acidic group and/or esters of these acid monomers and/or amides of these acid monomers.

Monomers bearing an acidic group which may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acid monomers are advantageously selected from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates that may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters that are particularly preferred are the alkyl (meth)acrylates.

According to the present invention, the alkyl group of the esters may be either fluorinated or perfluorinated, i.e. some or all of the hydrogen atoms of the alkyl group are substituted by fluorine atoms.

Examples of amides of the acid monomers that may be mentioned are (meth)acrylamides, and especially N-alkyl (meth)acrylamides, in particular of a $C_2$-$C_{12}$ alkyl. Among the N-alkyl(meth)acrylamides that may be mentioned are N-ethylacrylamide, N-t-butylacrylamide, N-t-octylacrylamide and N-undecylacrylamide.

The vinyl film-forming polymers may also result from the homopolymerization or copolymerization of monomers selected from vinyl esters and styrene monomers. In particular, these monomers may be polymerized with acid monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and alpha-methylstyrene.

Among the film-forming polycondensates that may be mentioned are polyurethanes, polyesters, polyesteramides, polyamides, epoxy ester resins and polyureas.

The polyurethanes may be selected from anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, in particular diols.

The dicarboxylic acid may be aliphatic, alicyclic or aromatic. Examples of such acids that may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbomanedicarboxylic acid, diglycolic acid, thiodipropionic acid, 2,5-naphthalenedicarboxylic acid or 2,6-naphthalenedicarboxylic acid. These dicarboxylic acid monomers may be used alone or as a combination of at least two dicarboxylic acid monomers. Among these monomers, the ones preferentially selected are phthalic acid, isophthalic acid and terephthalic acid.

The diol may be selected from aliphatic, alicyclic and aromatic diols. The diol used is preferably selected from: ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

The polyester may also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in particular.

The aromatic nucleus of the difunctional aromatic monomer also bearing a group —$SO_3M$ as described above may be selected, for example, from benzene, naphthalene, anthracene, biphenyl, oxybiphenyl, sulphonylbiphenyl and methylenebiphenyl nuclei. As examples of difunctional aromatic monomers also bearing a group —$SO_3M$, mention may be made of: sulphoisophthalic acid, sulphoterephthalic acid, sulphophthalic acid, 4-sulphonaphthalene-2,7-dicarboxylic acid.

The copolymers preferably used are those based on isophthalate/sulphoisophthalate, and more particularly copolymers obtained by condensation of diethylene glycol, cyclohexanedimethanol, isophthalic acid and sulphoisophthalic acid.

The polymers of natural origin, optionally modified, may be selected from shellac resin, sandarac gum, dammar resins, elemi gums, copal resins and cellulosic polymers, and mixtures thereof.

According to a first embodiment of the invention, the film-forming polymer may be a water-soluble polymer and may then be present in the continuous aqueous phase of an emulsion according to the invention.

According to another variant, the film-forming polymer may be a polymer dissolved in a liquid fatty phase comprising organic solvents or oils such as those described later on (the film-forming polymer is thus said to be a lipid-soluble polymer). The liquid fatty phase preferably comprises a volatile oil, optionally mixed with a non-volatile oil, the oils possibly being selected from those mentioned below.

Examples of lipid-soluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of these copolymers that may be mentioned are the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of lipid-soluble film-forming polymers that may also be mentioned are lipid-soluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such lipid-soluble copolymers may be selected from copolymers of polyvinyl stearate, of polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly(meth)acrylates to be crosslinked with the aid of ethylene glycol dimethacrylate or tetraethylene glycol dimethacrylate.

The lipid-soluble copolymers defined above are known and are described in particular in patent application FR-A-2 232 303; they may have a weight-average molecular weight ranging from 2000 to 500 000 and preferably from 4000 to 200 000.

Mention may also be made of lipid-soluble homopolymers, and in particular those resulting from the homopolymerization of vinyl esters containing from 9 to 22 carbon atoms or of alkyl acrylates or methacrylates, the alkyl radicals containing from 2 to 24 carbon atoms.

Examples of lipid-soluble homopolymers that may especially be mentioned include: polyvinyl laurate and polylauryl (meth)acrylates, these poly(meth)acrylates possibly being crosslinked using ethylene glycol dimethacrylate or tetraethylene glycol dimethacrylate.

According to one advantageous embodiment, a composition according to the invention comprises at least one polyvinyl laurate film-forming polymer.

As lipid-soluble film-forming polymers which may be used in the invention, mention may also be made of polyalkylenes and in particular copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers which may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Mention may also be made of silicone resins, which are generally soluble or swellable in silicone oils, which are crosslinked polyorganosiloxane polymers. The nomenclature of silicone resins is known under the name "MDTQ", the resin being described as a function of the various siloxane monomer units it comprises, each of the letters "MDTQ" characterizing a type of unit.

Examples of commercially available polymethylsilsesquioxane resins that may be mentioned include those sold by the company Wacker under the reference Resin MK, such as Belsil PMS MK, and by the company Shin-Etsu under the reference KR-220L.

Siloxysilicate resins that may be mentioned include trimethylsiloxysilicate (TMS) resins such as those sold under the reference SR1000 by the company General Electric or under the reference TMS 803 by the company Wacker. Mention may also be made of the trimethylsiloxysilicate resins sold in a solvent such as cyclomethicone, sold under the name KID-7312) by the company Shin-Etsu, and DC 749 and DC 593 by the company Dow Corning.

Mention may also be made of silicone resin copolymers such as those mentioned above with polydimethylsiloxanes, for instance the pressure-sensitive adhesive copolymers sold by the company Dow Corning under the reference Bio-PSA and described in document U.S. Pat. No. 5,162,410, or the silicone copolymers derived from the reaction of a silicone resin, such as those described above, and of a diorganosiloxane, as are described in document WO 2004/073626.

It is also possible to use silicone polyamides of polyorganosiloxane type, such as those described in documents U.S. Pat. No. 5,874,069, U.S. Pat. No. 5,919,441, U.S. Pat. No. 6,051,216 and U.S. Pat. No. 5,981,680.

These silicone polymers may belong to the two following classes:
 polyorganosiloxanes containing at least two groups capable of forming hydrogen interactions, these two groups being situated in the chain of the polymer, and/or
 polyorganosiloxanes containing at least two groups capable of forming hydrogen interactions, these two groups being situated on grafts or branches.

According to one embodiment of the invention, the film-forming polymer is a film-forming linear block ethylenic polymer, which preferably comprises at least a first block and at least a second block with different glass transition temperatures (Tg), said first and second blocks being linked together via an intermediate block comprising at least one constituent monomer of the first block and at least one constituent monomer of the second block.

Advantageously, the first and second blocks of the block polymer are mutually incompatible.

Such polymers are described, for example, in document EP 1 411 069 or WO 04/028488.

The film-forming polymer may also be present in a composition of the invention in the form of particles dispersed in an aqueous phase or in a non-aqueous solvent phase, which is generally known as a latex or pseudolatex. The techniques for preparing these dispersions are well known to those skilled in the art.

Aqueous dispersions of film-forming polymers that may be used include the acrylic dispersions sold under the names Neocryl XK-90°, Neocryl A1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760° by the company Interpolymer, Allianz OPT by the company Rohm & Haas, aqueous dispersions of acrylic or styrene/acrylic polymers sold under the brand name Joncryl® by the company Johnson Polymer, or the aqueous dispersions of polyurethane sold under the names Neorez R-981° and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulphopolyesters sold under the brand name Eastman AQ® by the company Eastman Chemical Products, and vinyl dispersions, for instance Mexomer PAM® from the company Chimex, and mixtures thereof.

Examples of non-aqueous film-forming polymer dispersions that may also be mentioned include acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055081.

A composition according to the invention may also further comprise a plasticizer that promotes the formation of a film with the film-forming polymer. Such a plasticizer may be selected from any compound known to those skilled in the art as being capable of fulfilling the desired function.

Gellants

A composition of the invention may also comprise at least one hydrophilic or water-soluble gellant.

Hydrophilic or water-soluble gellants that may be mentioned include:
 homopolymers or copolymers of acrylic or methacrylic acid or the salts and esters thereof, and in particular the products sold under the names Versicol F or Versicol K by the company Allied Colloid, Ultrahold 8 by the company Ciba-Geigy, and the polyacrylic acids of Synthalen K type;
 copolymers of acrylic acid and of acrylamide sold in the form of the sodium salt thereof under the names Reten by the company Hercules, sodium polymethacrylate sold under the name Darvan No. 7 by the company Vanderbilt, and the sodium salts of polyhydroxycarboxylic acids sold under the name Hydagen. F by the company Henkel;
 polyacrylic acid/alkyl acrylate copolymers of the Pemulen type;

AMPS (polyacrylamidomethylpropanesulphonic acid partially neutralized with ammonia and highly crosslinked) sold by the company Clariant;

AMPS/acrylamide copolymers of the Sepigel or Simulgel type, sold by the company SEPPIC, and AMPS/polyoxyethylenated alkyl methacrylate copolymers (crosslinked or non-crosslinked); and mixtures thereof.

As other examples of water-soluble gelling polymers, mention may be made of:

proteins, for instance proteins of plant origin, such as wheat or soybean proteins; proteins of animal origin such as keratins, for example keratin hydrolysates and sulphonic keratins;

anionic, cationic, amphoteric or nonionic chitin or chitosan polymers;

cellulose polymers such as hydroxyethylcellulose, hydroxypropylcellulose, methylcellulose, ethylhydroxyethylcellulose and carboxymethylcellulose, and also quaternized cellulose derivatives;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

associative polyurethanes such as the $C_{16}$—$OE_{120}$-$C_{16}$ polymer from the company Servo Delden (sold under the name Ser Ad FX1100, which is a molecule containing urethane functions and having a weight-average molecular weight of 1300), OE being an oxyethylene unit, Rheolate 205 containing urea functions, sold by the company Rheox, or Rheolate 208 or 204 (these polymers being sold in pure form) or DW 1206B from Rohm & Haas, containing a $C_{20}$ alkyl chain and a urethane bond, sold at a solids content of 20% in water. It is also possible to use solutions or dispersions of these associative polyurethanes, especially in water or in aqueous-alcoholic medium. Examples of such polymers that may be mentioned include Ser Ad FX1010, Ser Ad FX1035 and Ser Ad 1070 from the company Servo Delden, and Rheolate 255, Rheolate 278 and Rheolate 244 sold by the company Rheox. It is also possible to use the product DW 1206F and DW 1206J, and also Acrysol RM 184 or Acrysol 44 from the company Rohm & Haas, or Borchigel LW 44 from the company Borchers;

optionally modified polymers of natural origin, such as:
gum arabics, guar gum, xanthan derivatives and karaya gum;
alginates and carrageenans;
glycoaminoglycans, and hyaluronic acid and its derivatives;
shellac resin, sandarac gum, dammar resins, elemi gums and copal resins;
deoxyribonucleic acid;
mucopolysaccharides such as hyaluronic acid and chondroitin sulphates, and mixtures thereof.

Some of the water-soluble film-forming polymers cited earlier on above may also act as water-soluble gellants.

The hydrophilic gellants may be present in the compositions according to the invention in an amount from 0.05% to 40% by weight, preferably from 0.1% to 20% and better still from 0.5% to 15% by weight relative to the total weight of the composition.

Organic Solvents and Oils

The compositions according to the present patent application may also comprise at least one or two or more organic solvents or oils.

An "organic solvent or oil" in the sense of the patent application is a non-aqueous substance which is liquid at ambient temperature (25° C.) and atmospheric pressure (760 mmHg).

The oil may be selected from volatile oils and/or non-volatile oils, and mixtures thereof.

The oil or oils may be present in an amount of from 0.05% to 15% by weight, preferably from 0.1% to 10% by weight, relative to the total weight of the composition.

A "volatile oil" for the purposes of the invention is an oil which is able to evaporate on contact with the keratin substances in less than one hour at ambient temperature and atmospheric pressure. The volatile organic solvent or solvents and the volatile oils of the invention are organic solvents and volatile cosmetic oils which are liquid at ambient temperature and have a non-zero vapour pressure at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

In particular the volatile oils are selected from oils possessing an evaporation rate greater than or equal to 0.002 mg/cm²/min. The evaporation rate is measured as follows:

15 g of oil or of the mixture of oils to be tested are introduced into a crystallizing basin (diameter 7 cm) placed on a balance which is located within a chamber of approximately 0.3 m³ and whose temperature (25° C.) and hygrometry (relative humidity 50%) are regulated.

The liquid is left to evaporate freely, without agitation, with ventilation provided by a fan (rotary speed 2700 revolutions/minute and size 80×80×42 mm, for example the reference 8550 N from Papst-Motoren, the output corresponding to approximately 50 m³/hour) which is placed vertically above the crystallizing basin containing the solvent, the vanes being directed towards the crystallizing basin and at a distance of 20 cm from the base of the crystallizing basin.

The mass of oil remaining in the crystallizing basin is measured at regular intervals. The evaporation rates are expressed in mg of oil evaporated per unit surface area (cm²) and per unit time (minute).

A "non-volatile oil" is an oil which remains on the keratin substances at ambient temperature and atmospheric pressure for at least a number of hours and which has more particularly a vapour pressure of less than $10^{-3}$ mmHg (0.13 Pa).

These oils may be hydrocarbon oils, silicone oils, fluoro oils, or mixtures thereof.

A "hydrocarbon oil" is an oil containing principally hydrogen and carbon atoms and optionally oxygen, nitrogen, sulphur and/or phosphorus atoms. The volatile hydrocarbon oils may be selected from hydrocarbon oils having 8 to 16 carbon atoms, and more particularly $C_8$-$C_{16}$ branched alkanes such as the $C_8$-$C_{16}$ isoalkanes of petroleum origin (also called isoparaffins) such as isododecane (also called 2,2,4,4,6-pentamethyl-heptane), isodecane and isohexadecane, and, for example, the oils sold under the trade names Isopars or Permetyls, branched $C_8$-$C_{16}$ esters, isohexyl neopentanoate, and mixtures thereof. Other volatile hydrocarbon oils may also be used, such as the petroleum distillates, more particularly those sold under the name Shell Solt by Shell. The volatile solvent is preferably selected from volatile hydrocarbon oils having 8 to 16 carbon atoms, and mixtures thereof.

Further volatile oils which can be used are the volatile silicones, such as, for example, volatile linear or cyclic silicone oils, more particularly those having a viscosity ≤ 8 centistokes ($8 \times 10^{-6}$ m$^2$/s), and having more particularly 2 to 7 silicon atoms, these silicones optionally comprising alkyl or alkoxy groups having 1 to 10 carbon atoms. Possible volatile silicone oils which can be used in the invention include, more particularly, octamethylcyclotetrasiloxane, decamethylcyclopentasiloxane, dodeca-methylcyclohexasiloxane, beptamethylhexyltrisiloxane, heptamethyloctyltrisiloxane, hexamethyldisiloxane, octamethyltrisiloxane, decamethyltetrasiloxane, dodecamethylpentasiloxane and mixtures thereof.

It is also possible to use volatile fluorine-containing solvents such as nonafluoromethoxybutane or perfluoro-methylcyclopentane.

The composition may further comprise at least one non-volatile organic solvent or oil, selected more particularly from non-volatile hydrocarbon oils and/or silicone oils and/or fluoro oils.

Possible non-volatile hydrocarbon oils include more particularly:

hydrocarbon oils of plant origin such as the triesters of fatty acids and glycerol, in which the fatty acids may have varied chain lengths from $C_4$ to $C_{24}$, these chains being linear or branched and saturated or unsaturated; these oils are more particularly wheatgerm oil, sunflower oil, grapeseed oil, sesame oil, maize oil, apricot oil, castor oil, karite oil, avocado oil, olive oil, soya oil, sweet almond oil, palm oil, rapeseed oil, cotton oil, hazelnut oil, macadamia oil, jojoba oil, alfalfa oil, poppy oil, pumpkin oil, marrow oil, blackcurrant oil, evening primrose oil, millet oil, barley oil, quina oil, rye oil, safflower oil, candlenut oil, passionflower oil or musk rose oil; or else caprylic/capric acid triglycerides, such as those sold by Stéarineries Dubois or those sold under the names Miglyol 810, 812 and 818 by Dynamit Nobel, synthetic ethers having 10 to 40 carbon atoms;

linear or branched hydrocarbons of mineral or synthetic origin, such as petroleum jelly, polydecenes, hydrogenated polyisobutene such as Parleam, and squalane, and mixtures thereof;

synthetic esters such as the oils of formula $R_1COOR_2$ in which $R_1$ represents the residue of a linear or branched fatty acid containing 1 to 40 carbon atoms and $R_2$ represents a hydrocarbon chain, more particularly a branched hydrocarbon chain, containing 1 to 40 carbon atoms, with the proviso that $R_1+R_2$ is ≥10, such as, for example, Purcellin oil (cetostearyl octanoate), isopropyl myristate, isopropyl palmitate, $C_{12}$ to $C_{15}$ alcohol benzoate, hexyl laurate, diisopropyl adipate, isononyl isononanoate, 2-ethylhexyl palmitate, isostearyl isostearate, octanoates, decanoates or ricinoleates of alcohols or of polyalcohols, such as propylene glycol dioctanoate; hydroxyl-containing esters such as isostearyl lactate and diisostearyl malate; and pentaerythritol esters;

fatty alcohols which are liquid at ambient temperature and have a branched and/or unsaturated carbon chain having 12 to 26 carbon atoms, such as octyldodecanol, isostearyl alcohol, oleyl alcohol, 2-hexyldecanol, 2-butyloctanol and 2-undecylpenta-decanol;

higher fatty acids such as oleic acid, linoleic acid and linolenic acid;

carbonates, acetals, citrates, and mixtures thereof.

The non-volatile silicone oils which can be used in the composition according to the invention may be non-volatile polydimethylsiloxanes (PDMS), polydimethylsiloxanes containing alkyl or alkoxy groups pendantly and/or at the end of the silicone chain, these groups each having 2 to 24 carbon atoms, or phenyl silicones such as phenyltrimethicones, phenyldimethicones, phenyltrimethylsiloxydiphenylsiloxanes, diphenyldimethicones, diphenylmethyldiphenyltrisiloxanes and 2-phenylethyl trimethylsiloxysilicates.

The fluoro oils which can be used in the invention are more particularly fluorosilicone oils, fluorine-containing polyethers and fluorosilicones as described in document EP-A-847752.

Colorants

The composition according to the invention may further comprise at least one colorant selected, for example, from pigments, nacres, dyes and effect materials and mixtures thereof.

These colorants may be present in an amount of from 0.01% to 30% by weight, relative to the total weight of the composition.

The pigments that are useful in the present invention may be in the form of powder or of pigmentary paste.

The term "dyes" should be understood as meaning compounds, generally organic, which are soluble in at least one oil or in an aqueous-alcoholic phase.

The term "pigments" should be understood as meaning white or coloured, mineral or organic particles, which are insoluble in an aqueous medium, and which are intended to colour and/or opacify the resulting film.

The term "nacres" or nacreous pigments should be understood as meaning coloured particles of any form, which may or may not be iridescent, especially those produced by certain molluscs in their shell or else synthesized, and which have a colour effect via optical interference.

The pigment may be an organic pigment. The term "organic pigment" means any pigment that satisfies the definition in Ullmann's encyclopaedia in the chapter on organic pigments. The organic pigment may especially be selected from nitroso, nitro, azo, xanthene, quinoline, anthraquinone, phthalocyanine, metal complex, isoindolinone, isoindoline, quinacridone, perinone, perylene, diketopyrrolopyrrole, thioindigo, dioxazine, triphenylmethane and quinophthalone compounds.

The organic pigment(s) may be selected, for example, from carmine, carbon black, aniline black, melanin, azo yellow, quinacridone, phthalocyanine blue, sorghum red, the blue pigments codified in the Colour Index under the references CI 42090, 69800, 69825, 73000, 74100 and 74160, the yellow pigments codified in the Colour Index under the references CI 11680, 11710, 15985, 19140, 20040, 21100, 21108, 47000 and 47005, the green pigments codified in the Colour Index under the references CI 61565, 61570 and 74260, the orange pigments codified in the Colour Index under the references CI 11725, 15510, 45370 and 71105, the red pigments codified in the Colour Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

These pigments may also be in the form of composite pigments as described in patent EP 1 184 426. These composite pigments may be composed especially of particles comprising an inorganic nucleus at least partially coated with an organic pigment and at least one binder to fix the organic pigments to the nucleus.

The pigment may also be a lake. The term "lake" means insolubilized dyes adsorbed onto insoluble particles, the assembly thus obtained remaining insoluble during use.

The inorganic substrates onto which the dyes are adsorbed are, for example, alumina, silica, calcium sodium borosilicate or calcium aluminium borosilicate, and aluminium.

Among the organic dyes, mention may be made of cochineal carmine. Mention may also be made of the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

An example of a lake that may be mentioned is the product known under the following name: D&C Red 7 (CI 15 850:1).

The pigment may be a mineral pigment. The term "mineral pigment" means any pigment that satisfies the definition in Ullmann's encyclopaedia in the chapter on inorganic pigments. Among the mineral pigments that are useful in the present invention, mention may be made of zirconium oxide or cerium oxide, and also iron oxide or chromium oxide, manganese violet, ultramarine blue, chromium hydrate, ferric blue and titanium dioxide. The following mineral pigments may also be used: $Ta_2O_5$, $Ti_3O_5$, $Ti_2O_3$, TiO, $ZrO_2$ as a mixture with $TiO_2$, $ZrO_2$, $Nb_2O_5$, $CeO_2$, ZnS.

The pigment may also be a pigment with special effects. The term "pigments with special effects" means pigments that generally create a non-uniform coloured appearance (characterized by a certain shade, a certain vivacity and a certain lightness) that changes as a function of the conditions of observation (light, temperature, observation angles, etc.). They thus contrast with white or coloured pigments that afford a standard uniform opaque, semi-transparent or transparent shade.

Two types of pigment with special effects exist: those with a low refractive index, such as fluorescent, photochromic or thermochromic pigments, and those with a high refractive index, such as nacres or flakes.

Pigments with special effects that may be mentioned include nacreous pigments such as white nacreous pigments such as mica coated with titanium or with bismuth oxychloride, coloured nacreous pigments such as titanium mica with iron oxides, titanium mica especially with ferric blue or with chromium oxide, titanium mica with an organic pigment of the abovementioned type, and also nacreous pigments based on bismuth oxychloride.

Mention may also be made of pigments with an interference effect that are not fixed onto a substrate, for instance liquid crystals (Helicons FTC from Wacker), holographic interference flakes (Geometric Pigments or Spectra fix from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductive nanoparticles capable of emitting, under light excitation, irradiation with a wavelength of between 400 nm and 700 nm. These nanoparticles are known from the literature. They may be manufactured in particular according to the processes described, for example, in U.S. Pat. No. 6,225,198 or U.S. Pat. No. 5,990,479, in the publications cited therein, and also in the following publications: Dabboussi B. O. et al. "(CdSe) ZnS core-shell quantum dots: synthesis and characterization of a size series of highly luminescent nanocrystallites" *Journal of Physical Chemistry B*, vol. 101, 1997, pp. 9463-9475 and Peng, Xiaogang et al. "Epitaxial growth of highly luminescent CdSe/CdS core/shell nanocrystals with photostability and electronic accessibility", *Journal of the American Chemical Society*, vol. 119, no. 30, pp. 7019-7029.

Pigments with special effects also comprise fluorescent pigments, whether these are substances that are fluorescent in daylight or that produce an ultraviolet fluorescence, phosphorescent pigments, photochromic pigments and thermochromic pigments.

The pigment may also be a nacreous pigment such as white nacreous pigments, for example mica coated with titanium or with bismuth oxychloride, coloured nacreous pigments such as mica coated with titanium and with iron oxides, mica coated with titanium and especially with ferric blue or chromium oxide, mica coated with titanium and with an organic pigment as defined above, and also nacreous pigments based on bismuth oxychloride. Examples that may be mentioned include the Cellini pigments sold by Engelhard (Mica-$TiO_2$-lake), Prestige sold by Eckart (Mica-$TiO_2$) or Colorona sold by Merck (Mica-$TiO_2$—$Fe_2O_3$).

In addition to nacres on a mica support, multilayer pigments based on synthetic substrates such as alumina, silica, calcium sodium borosilicate or calcium aluminium borosilicate, and aluminium, may be envisaged.

The size of the pigment that is useful in the context of the present invention is generally between 10 nm and 200 ∞m, preferably between 20 nm and 80 μm and more preferentially between 30 nm and 50 μm.

The pigments may be dispersed in the product by means of a dispersant.

The dispersant serves to protect the dispersed particles against agglomeration or flocculation. This dispersant may be a surfactant, an oligomer, a polymer or a mixture of several thereof, bearing one or more functionalities with strong affinity for the surface of the particles to be dispersed. In particular, they can physically or chemically attach to the surface of the pigments. These dispersants also contain at least one functional group that is compatible with or soluble in the continuous medium. In particular, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxaneioxypropylene mixtures such as those sold by the company Dow Corning under the references DC2-5185 and DC2-5225 C.

The polydihydroxystearic acid and the 12-hydroxystearic acid esters are preferably intended for a hydrocarbon-based or fluorinated medium, whereas the mixtures of oxyethylenetoxypropylenated dimethylsiloxane are preferably intended for a silicone medium.

Coated Pigments

According to one particularly advantageous embodiment, the composition comprises at least one pigment coated with at least one lipophilic compound, said pigment being particularly selected from organic pigments, composite pigments, lakes and mineral pigments, as described above.

The coating may also comprise at least one additional, non-lipophilic compound.

For the purposes of the invention, the "coating" of a pigment according to the invention denotes, generally, the total or partial surface treatment of the pigment with a surface agent, which is absorbed, adsorbed or grafted onto said pigment.

The surface-treated pigments may be prepared by chemical, electronic, mechanochemical or mechanic surface treatment techniques that are well known to a person skilled in the art. Also possible is the use of commercial products.

The surface agent may be absorbed, adsorbed or grafted onto the pigments by evaporation of solvent, chemical reaction and creation of a covalent bond.

In one version the surface treatment consists of a solid particle coating.

The coating may represent from 0.1 to 20% by weight, and more particularly from 0.5% to 5% by weight, of the total weight of the coated pigment.

Coating may be carried out, for example, by adsorption of a liquid surface agent onto the surface of the solid particles, by simple mixing, with stirring, of the particles and of said surface agent, optionally with heat, prior to the incorporation of the particles into the other ingredients of the care or makeup composition.

Coating may be carried out, for example, by chemical reaction of a surface agent with the surface of the solid pigment particles, and creation of a covalent bond between the surface agent and the particles. This method is described in particular in U.S. Pat. No. 4,578,266.

The chemical surface treatment may involve diluting the surface agent in a volatile solvent, dispersing the pigments in this mixture, then slowly evaporating the volatile solvent, to cause the surface agent to deposit on the surface of the pigments.

Hydrophobic or Lipophilic Treatment Agent

When the pigment comprises a lipophilic coating, the latter is present n the fatty phase of the composition according to the invention.

According to one particular embodiment of the invention, the pigments may be coated in accordance with the invention with at least one compound selected from silicone surface agents; fluorinated surface agents; fluorosilicone surface agents; metal soaps, N-acylamino acids or their salts; lecithin and its derivatives; isopropyl triisostearyltitanate; isostearyl sebacate; natural plant or animal waxes, polar synthetic waxes; fatty esters; and phospholipids, and mixtures thereof.

Silicone Surface Agent

According to one particular embodiment, the pigments may be totally or partially surface treated with a compound of silicone type.

Silicone surface agents may be selected from organopolysiloxanes, silane derivatives, silicone-acrylate copolymers, silicone resins, and mixtures thereof.

An "organopolysiloxane compound" is a compound having a structure comprising an alternation of silicon atoms and oxygen atoms, and comprising organic radicals bonded to the silicon atoms.

i) Non-Elastomeric Organopolysiloxane

Non-elastomeric organopolysiloxanes include, in particular, polydimethylsiloxanes, polymethyihydrosiloxanes and polyalkoxydimethylsiloxanes.

The alkoxy group may be represented by the radical R—O— such that R represents methyl, ethyl, propyl, butyl or octyl, 2-phenylethyl, 2-phenylpropyl or 3,3,3-trifluoropropyl radicals, aryl radicals such as phenyl, tolyl and xylyl, or substituted aryl radicals such as phenylethyl.

A method which allows the pigments to be surface treated with a polymethylhydrosiloxane involves dispersing the pigments in an organic solvent and then adding the silicone compound. By heating of the mixture, covalent bonds are formed between the silicone compound and the surface of the pigment.

According to one preferred embodiment, the silicone surface agent may be a non-elastomeric organopolysiloxane, selected in particular from polydimethylsiloxanes.

ii) Alkylsilanes and Alkoxysilanes

Silanes with alkoxy functionality are described in particular by Witucki in "A silane primer, Chemistry and applications of alkoxy silanes", Journal of Coatings Technology, 65, 822, pages 57-60, 1993.

Alkoxysilanes such as the alkyltriethoxysilanes and the alkyltrimethoxysilanes that are sold under the names Silquest A-137 (OSI Specialties) and Prosil 9202 (PCR) may be used for coating the pigments.

The use of the alkylpolysiloxanes having a terminal reactive groups such as alkoxy, hydroxyl, halogen, amino or imino is described in patent application JP H07-196946. They are also suitable for treating the pigments.

iii) Silicone-Acrylate Polymers

Grafted silicone-acrylic polymers having a silicone backbone, as are described in U.S. Pat. No. 5,725,882, U.S. Pat. No. 5,209,924, U.S. Pat. No. 4,972,037, U.S. Pat. No. 4,981,903, U.S. Pat. No. 4,981,902, U.S. Pat. No. 5,468,477, and in U.S. Pat. No. 5,219,560 and EP 0 388 582, may be used.

Other silicone-acrylate polymers may be silicone polymers comprising in their structure the unit of formula (I) below:

$$\begin{array}{c} G_1 \\ | \\ -\!\!\!-\!\!(\mathrm{Si}-\!\!\mathrm{O})_a\!\!-\!\!(\mathrm{Si}-\!\!\mathrm{O})_b\!\!-\!\!(\mathrm{Si}-\!\!\mathrm{O})_c\!\!-\!\! \\ | \quad\quad | \quad\quad | \\ (G_2)_n\text{-S-}G_3 \quad G_1 \quad (G_2)_m\text{-S-}G_4 \end{array} \quad (I)$$

in which the radicals $G_1$, which are identical or different, represent hydrogen or a $C_1$-$C_{10}$ alkyl radical or else a phenyl radical; the radicals $G_2$, which are identical or different, represent a $C_1$-$C_{10}$ alkylene group; $G_3$ represents a polymeric residue resulting from the (homo)polymerization of at least one ethylenically unsaturated anionic monomer; $G_4$ represents a polymeric residue resulting from the (homo)polymerization of at least one ethylenically unsaturated hydrophobic monomer; m and n are 0 or 1; a is an integer from 0 to 50; b is an integer which may be between 10 and 350, and c is an integer from 0 to 50; with the proviso that one of the parameters a and c is other than 0.

The unit of the formula (I) above has preferably at least one, and more preferably all, of the following features:
- the radicals $G_1$ denote an alkyl radical, preferably the methyl radical;
- n is not zero, and the radicals $G_2$ represent a divalent $C_1$-$C_3$ radical, preferably a propylene radical;
- $G_3$ represents a polymeric radical resulting from the (homo)polymerization of at least one ethylenically unsaturated carboxylic acid monomer, preferably acrylic acid and/or methacrylic acid; and
- $G_4$ represents a polymeric radical resulting from the (homo)polymerization of at least one ($C_1$-$C_{10}$)alkyl (meth)acrylate monomer, preferably methyl or isobutyl (meth)acrylate.

Examples of silicone polymers conforming to the formula (I) are, in particular, polydimethylsiloxanes (PDMS) which are grafted, via a thiopropylene linker element, with mixed polymeric units of poly(meth)acrylic acid type and of polymethyl (meth)acrylate type.

Other examples of silicone polymers conforming to the formula (I) are, in particular, polydimethylsiloxanes (PDMS) grafted, via a thiopropylene linker element, with polymeric units of the polyisobutyl (meth)acrylate type.

iv) Silicone Resins

The silicone surface agent may be selected from silicone resins.

By "resin" is meant a three-dimensional structure.

The silicone resins may be soluble or swellable in silicone oils. These resins are crosslinked polyorganosiloxane polymers.

The nomenclature of silicone resins is known by the name "MDTQ", the resin being described by way of the different siloxane monomer units it comprises, with each of the letters 1 "MDTQ" characterizing one type of unit.

The letter M represents the monofunctional unit of formula $(CH_3)_3SiO_{1/2}$, the silicon atom being joined to a single oxygen atom in the polymer comprising this unit.

The letter D signifies a difunctional unit $(CH_3)_2SiO_{2/2}$, in which the silicon atom is joined to two oxygen atoms.

The letter T represents a trifunctional unit of formula $(CH_3)SiO_{3/2}$.

In the units M, D and T defined above, at least one of the methyl groups may be substituted by a group R other than the methyl group, such as a hydrocarbon (more particularly alkyl) radical having from 2 to 10 carbon atoms, or a phenyl group, or else a hydroxyl group.

Lastly, the letter Q signifies a tetrafunctional unit $SiO_{4/2}$, in which the silicon atom is bonded to four hydrogen atoms which are themselves bonded to the rest of the polymer.

Various resins with different properties may be obtained on the basis of these different units, the properties of these polymers varying depending on the type of monomers (or units), the type and number of substituted radicals, the length of the polymeric chain, the degree of branching, and the size of the pendant chains.

Examples of these silicone resins include:
siloxysilicates, which may be trimethylsiloxysilicates of formula $[(CH_3)_3XSiXO]_xX(SiO_{4/2})_y$ (MQ units), in which x and y are integers from 50 to 80,
polysilsesquioxanes of formula $(CH_3SiO_{3/2})_x$ (T units) in which x is greater than 100, and in which at least one of the methyl radicals may be substituted by a group R as defined above,
polymethylsilsesquioxanes, which are polysilsesquioxanes in which none of the methyl radicals is substituted, by another group. Polymethylsilsesquioxanes of this kind are described in document U.S. Pat. No. 5,246,694, the content of which is incorporated by reference.

Examples of commercially available polymethylsilsesquioxane resins include those sold:
by the company Wacker under the name Resin MK, such as Belsil PMS MK: a polymer comprising repeating $CH_3SiO_{3/2}$ units (T units), which may also comprise up to 1% by weight of $(CH_3)_2SiO_{2/2}$ units (D units), and has an average molecular weight of approximately 10 000,
by the company Shin-Etsu under the names KR-220L, these being composed of T units of formula $CH_3SiO_{3/2}$ and having terminal Si—OH (silanol) groups, or under the name KR-242A, comprising 98% of T units and 2% of dimethyl D units and having terminal Si—OH groups,
or else under the name KR-251, comprising 88% of T units and 12% of dimethyl D units and having terminal Si—OH groups.

Siloxysilicate resins include trimethylsiloxysilicate (TMS) resins, optionally in powder form. Such resins are sold under the names SR1000, .E. 1 170-002 or SS 4230 by the company General Electric, or under the names TMS 803 and Wacker 803 and 804 by the company Wacker Silicone Corporation.

Mention may also be made of trimethylsiloxysilicate resins sold in a solvent such as cyclomethicone, which are sold under the name KF-7312.1 by the company Shin-Etsu or DC 749 and DC 593 by the company Dow Corning.

Examples of commercial names of pigments treated with a silicone compound include the following:
red iron oxide/dimethicone, sold under the name SA-C 338075-10 by Miyoshi Kasei,
a pigment obtained by treating DC Red 7 with a silicone compound, as sold by the company Coletica under the name Gransil GCM (which is a mixture of D5 and polysilicone 11).

Fluorinated Surface Agent

The pigments may be totally or partially surface treated with a compound of fluorinated type.

Fluorinated surface agents may be selected from perfluoroalkyl phosphates, perfluoropolyethers, polytetrafluoropolyethylenes (PTFE), perfluoroalkanes, perfluoroalkylsilazanes, polyhexafluoropropylene oxides and polyorganosiloxanes comprising perfluoroalkyl perfluoropolyether groups.

A "perfluoroalkyl radical" is an alkyl radical in which all of the hydrogen atoms have been replaced by fluorine atoms.

Perfluoropolyethers are described in particular in patent application EP-A-486135, and sold in particular under the Fomblin trade names by the company Montefluos.

Perfluoroalkyl phosphates are described more particularly in patent application JP H05-86984. The perfluoroalkyl diethanolamine phosphates sold by Asahi Glass under the name AsahiGuard AG530 may be used.

Among the linear perfluoroalkanes, mention may be made of perfluorocycloalkanes, perfluoro(alkylcycloalkanes), perfluoropolycycloalkanes, perfluorinated aromatic hydrocarbons (perfluoroarenes), and perfluorinated organic hydrocarbon compounds comprising at least one heteroatom.

The perfluoroalkanes include the series of the linear alkanes such as perfluorooctane, perfluorononane or perfluorodecane.

The perfluorocycloalkanes and perfluoro(alkylcycloalkanes) include the perfluorodecalin sold under the name Flutec PPS GMP by the company Rhodia, perfluoro(methyldecalin), and perfluoro($C_3$-$C_5$ alkylcyclohexanes) such as perfluoro(butylcyclohexane).

The perfluoropolycycloalkanes include bicyclo[3.3.1] nonane derivatives such as perfluorotrimethylbicyclo[3.3.1] nonane, adamantane derivatives such as perfluorodimethyladamantane, and perfluorinated derivatives of hydrogenated phenanthrene, such as tetracosafluorotetradecahydrophenanthrene.

The perfluoroarenes include perfluorinated naphthalene derivatives such as perfluoronaphthalene and perfluoro-1-methylnaphthalene.

Examples of commercial names of pigments treated with a fluoro compound include:
the yellow iron oxide/perfluoroalkyl phosphate sold under the name PF 5 Yellow 601 by the company Daito Kasei,
the red iron oxide/perfluoroalkyl phosphate sold under the name PP 5 Red R 5161, by the company Daito Kasei, the black iron oxide/perfluoroalkyl phosphate sold under the name PF 5 Black BL 100 by the company Daito Kasei, the titanium dioxide/perfluoroalkyl phosphate sold under the name PF 5 TiO2 CR 50 by the company Daito Kasei, the yellow iron oxide/perfluoropolymethyl isopropyl ether sold under the name Iron Oxide Yellow BF-25-3 by the company Toshiki, the DC Red 7/perfluoropolymethyl isopropyl ether sold under the name D&C Red 7 FHC by the company Cardre Inc., the DC Red 6/PTFE sold under the name T 9506 by the company Warner-Jenkinson.

Fluorosilicone Surface Agent

The pigments may be totally or partially surface treated with a compound of fluorosilicone type.

The fluorosilicone compound may be selected from perfluoroalkyldimethicones, perfluoroalkylsilanes and perfluoroalkyltrialkoxysilanes.

Perfluoroalkylsilanes include the products LP-IT and LP-4T sold by Shin-Etsu Silicone.

The perfluoroalkyldimethicones may be represented by the following formula:

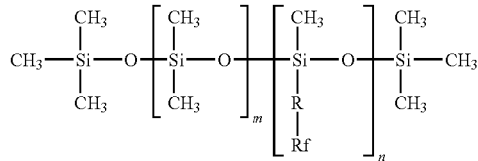

in which:

R represents a linear or branched divalent alkyl group having 1 to 6 carbon atoms, preferably a divalent methyl, ethyl, propyl or butyl group, Rf represents a perfluoroalkyl radical having 1 to 9 carbon atoms, preferably 1 to 4 carbon atoms, m is selected between 0 to 150, preferably from 20 to 100, and n is selected between 1 to 300, preferably from 1 to 100.

Examples of commercial names of pigments treated with a fluorosilicone compound include the titanium dioxide/fluorosilicone sold under the name Fluorosil Titanium Dioxide 100TA by the company Advanced Dermaceuticals International Inc.

Other Lipophilic Surface Agents

The hydrophobic treatment agent may also be selected from:

metal soaps, such as aluminium dimyristate and the aluminium salt of hydrogenated tallow glutamate.

Metal soaps include, in particular, the metal salts of fatty acids having from 12 to 22 carbon atoms and more particularly those having from 12 to 18 carbon atoms.

The metal of the metal soap may in particular be zinc or magnesium. As a metal soap, use may be made of zinc laurate, magnesium stearate, magnesium myristate, zinc stearate, and mixtures thereof.

The fatty acid may in particular be selected from lauric acid, myristic acid, stearic acid and palmitic acid.

N-acylamino acids or their salts, which may comprise an acyl group having from 8 to 22 carbon atoms, such as, for example, a 2-ethylhexanoyl, caproyl, lauroyl, myristoyl, palmitoyl, stearoyl or cocoyl group.

The amino acid may be, for example, lysine, glutamic acid or alanine.

The salts of these compounds may be aluminium, magnesium, calcium, zirconium, zinc, sodium or potassium salts.

Accordingly, in one particularly preferred embodiment, an N-acylamino acid derivative may be in particular a glutamic acid derivative and/or a salt thereof, and more particularly a stearoylglutamate, such as, for example, aluminium stearoylglutamate.

lecithin and its derivatives, isopropyl triisostearyltitanate.

Examples of pigments treated with isopropyl titanium triisostearate (ITT) include those sold under the trade name BWBO-I2 (Iron oxide CI77499 and isopropyl titanium triisostearate), BWYO-I2 (Iron oxide CI77492 and isopropyl titanium triisostearate) and BWRO-I2 (Iron oxide CI77491 and isopropyl titanium triisostearate) by the company KOBO.

isostearyl sebacate, natural plant or animal waxes or polar synthetic waxes, fatty esters, more particularly jojoba esters;

phospholipids, and mixtures thereof.

The waxes mentioned in the compounds indicated above may be those used generally in the cosmetics field, as defined below.

They may in particular be hydrocarbon, silicone and/or fluoro waxes, optionally comprising ester or hydroxyl functions. They may also be natural or synthetic in origin.

A "polar wax" is a wax containing chemical compounds comprising at least one polar group. The polar groups are well known to a person skilled in the art: they may be, for example, alcohol, ester or carboxylic acid groups. Not included among polar waxes are polyethylene waxes, paraffin waxes, microcrystalline waxes, ozokerite, and Fischer-Tropsch waxes.

More particularly, the polar waxes have an average Hansen solubility parameter dA at 25° C. such as dA>0 $(J/cm^3)^{1/2}$ and more preferably dA>1 $(J/cm^3)^{1/2}$.

$$\delta_a\sqrt{\delta_p^2+\delta_h^2}$$

where dP and dH are, respectively, the polar contributions and interaction-type contributions specific to the Hansen solubility parameters.

The definition of solvents in the three-dimensional solubility space according to Hansen is described in the article by C. M. Hansen: "The three dimensional solubility parameters", J. Paint Technol. 39, 105 (1967);

dH characterizes the forces of specific interactions (hydrogen bonds, acid/base, donor/acceptor, etc.);

dP characterizes the forces of Debye interactions between permanent dipoles and also the forces of Keesom interactions between induced dipoles and permanent dipoles.

The parameters dP and dH are expressed in $(J/cm^3)^{1/2}$.

A polar wax is composed in particular of molecules which, as well as carbon atoms and hydrogen atoms in their chemical structure, comprise heteroatoms (such as O, N and P).

Illustrative, non-limitative examples of these polar waxes include, in particular, natural polar waxes, such as beeswax, lanolin wax, orange wax, lemon wax, and Chinese insect waxes; rice bran wax, carnauba wax, candelilla wax, ouricury wax, cork fibre wax, sugarcane wax, Japan wax and sumac wax; and montan wax.

The pigments coated according to the invention with at least one lipophilic compound may be present in a composition of the invention in an amount of from 0.1% to 30% by weight, relative to the total weight of the composition, more preferably from 1% to 15% by weight.

According to one particular embodiment the pigments may be coated with at least one compound selected from silicone surface agents; fluorinated surface agents; N-acylamino acids or their salts; isopropyl triisostearyltitanate; natural plant or animal waxes; fatty esters; and mixtures thereof.

According to one particularly preferred embodiment the pigments may be coated with an N-acylamino acid and/or salt thereof, more particularly with a glutamic acid and/or a salt thereof, especially a stearoylglutamate, such as, for example, aluminium derivative stearoylglutamate, or with a fatty ester, more particularly with a jojoba ester.

Examples of pigments coated according to the invention include, more particularly, the following compounds:
- iron oxide coated with stearoylglutamate, for example sold by the company Miyoshi under the name NAI-C33-7001-10;
- iron oxide coated with jojoba esters, sold for example by the company Kobo under the name BWBO-NJE2; and
- titanium dioxide and iron oxide, which are coated with aluminium stearoylglutamate, sold for example under the name NAI by Miyoshi Kasei.

Fillers

The composition according to the invention may further comprise at least one filler.

The fillers may be mineral or organic and of any form, platelet-shaped, spherical or oblong, irrespective of the crystallographic form (for example lamellar, cubic, hexagonal, orthorhombic, etc.). Mention may be made of talc, mica, silica, silica surface-treated with a hydrophobic agent, kaolin, polyamide powder, for instance Nylon® (Orgasol® from Atochem), poly-β-alanine powder and polyethylene powder, tetrafluoroethylene polymer powders, (Teflon®), lauroyll-ysine, starch, boron nitride, hollow polymer microspheres such as those made of polyvinylidene chloride/acrylonitrile, for instance Expancel® (Nobel Industrie), acrylic acid copolymers (Polytrap® from Dow Corning) and silicone resin microbeads (for example Tospearls® from Toshiba), elastomeric polyorganosiloxane particles, precipitated calcium carbonate, magnesium carbonate, magnesium hydrocarbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

It is also possible to use a compound that is capable of swelling on heating, and especially heat-expandable particles such as non-expanded microspheres of copolymer of vinylidene chloride/acrylonitrile/methyl methacrylate or of acrylonitrile homopolymer copolymer, for instance those sold, respectively, under the references Expancel® 820 DU 40 and Expancel® 007WU by the company Akzo Nobel.

The fillers may represent from 0.1% to 25% and in particular from 0.2% to 20% by weight relative to the total weight of the composition.

Fibres

The compositions in accordance with the invention may further comprise at least one fibre, which allows, in particular, an improvement in the lengthening effect.

The term "fibre" should be understood as meaning an object of length L and diameter D such that L is greater than D, and preferably very much greater than D, D being the diameter of the circle in which the cross section of the fibre is inscribed. In particular, the ratio LID (or shape factor) is selected from the range from 3.5 to 2500, preferably from 5 to 500, and especially from 5 to 150.

The fibres that may be used in the composition of the invention may be mineral or organic fibres of synthetic or natural origin. They may be short or long, individual or organized, for example braided, and hollow or solid. They may have any shape, and may especially have a circular or polygonal (square, hexagonal or octagonal) cross section, depending on the specific application intended. In particular, their ends are blunt and/or polished to prevent injury.

In particular, the fibres have a length ranging from 1 μm to 10 mm, preferably from 0.1 mm to 5 min and better still from 0.3 mm to 3 mm. Their cross section may be within a circle of diameter ranging from 2 nm to 500 μm, preferably ranging from 100 nm to 100 μm and better still from 1 μm to 50 μm. The weight or linear density of the fibres is often given in denier or decitex, and represents the weight in grams per 9 km of yarn. Preferably, the fibres according to the invention may have a linear density selected from the range from 0.01 to 10 denier, preferably from 0.1 to 2 denier and better still from 0.3 to 0.7 denier.

The fibres that may be used in the compositions according to the invention may be selected from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in an amount of from 0.01% to 10% by weight, relative to the total weight of the composition, in particular from 0.1% to 5% by weight, and more particularly from 0.3 to 3% by weight.

A composition of the invention may further comprise any cosmetic active, such as actives selected from antioxidants, preservatives, fragrances, bactericidal or antiperspirant actives, neutralizing agents, emollients, moisturizers, thickeners, coalescents, plasticizers, vitamins, screens, particularly sunscreens, and mixtures thereof.

A person skilled in the art will of course ensure that any additional compounds and/or their amount are selected such that the advantageous properties of the composition according to the invention are not, or not substantially, adversely affected by the intended addition.

According to one preferred embodiment the composition according to the invention is a leave-in composition.

The composition according to the invention may be packaged in a container which delimits at least one compartment containing said composition, said container being closed by a closing element.

The container is preferably combined with an applicator, more particularly in the form of a brush comprising an arrangement of bristles held by a twisted wire. A twisted brush of this kind is described in particular in U.S. Pat. No. 4,887,622. It may also be in the form of a comb comprising a plurality of application elements, which are obtained in particular by moulding. Combs of this kind are described in, for example, patent FR 2 796 529. The applicator may be integral with the container, as is described in, for example, patent FR 2 761 959. The applicator is advantageously integral with a shaft which itself is integral with the closing element.

The closing element may be coupled to the container by screwing. Alternatively, coupling between the closing element and the container is accomplished other than by screwing, in particular via a bayonet mechanism, by snap fastening, or by tightening. By "snap fastening" is meant, in particular, any system involving the traversal of a rim or bead of material by elastic deformation of one portion, in particular of the closing element, followed by return to the elastically unstressed position of said portion after the rim or bead has been traversed.

The container may be at least partly made of thermoplastic material. Examples of thermoplastic materials include polypropylene or polyethylene.

Alternatively the container is made of non-thermoplastic material, especially of glass or of metal (or alloy).

The container is preferably fitted with a drainer which is located in the region of the opening of the container. A drainer of this kind makes it possible to wipe the applicator and, where appropriate, the shaft with which it may be integral. A drainer of this kind is described in, for example, patent FR 2 792 618.

The invention is illustrated in more detail in the examples below, which are given to illustrate, and not to limit, the invention.

EXAMPLES

Example 1

|   | Compounds/trade names | % by mass |
|---|---|---|
| A | Black iron oxide | 4 |
|   | Xanthan gum | 0.6 |
|   | Laponite (mixed magnesium/lithium/sodium silicate) | 0.6 |
|   | Deionized water | 58.8 |
|   | Denatured absolute ethyl alcohol | 8 |
|   | Monosodium salt of n-stearoyl-L-glutamic acid, (sold as Amisoft HS 11 by Ajinomoto) | 1 |
| B | Deodorized organic beeswax | 22 |
|   | Mixture of cetylstearylglucoside and cetyl and stearyl alcohols (20/80) (sold as Montanov 68 ® by SEPPIC) | 5 |
|   | TOTAL | 100 |

Procedure:

The thickeners, the glutamate surfactant and the colorants are dispersed with stirring in the aqueous phase. The phase A thus formed is then heated to 90° C. Phase A is then poured into the fatty phase, phase B, containing the waxes and the glucoside surfactant, at 90° C. Emulsification is carried out by stirring with a Moritz stirrer.

The emulsion is subsequently cooled to 60° C. with rotor/stator stirring, then to 25° C. with slow stirring by means of a flat blade.

The resultant wax-in-water emulsion has a pH of 6.7 and a viscosity, measured the day following its preparation, at 25° C., using a Rheomat 180 instrument from Lamy, fitted with an MS-R4 spindle, after 10 minutes of rotation at a speed of 200 rpm, of 5.4 Pa·s.

Example 2

|   | Compounds/trade names | % by mass |
|---|---|---|
| A | Black iron oxide | 7 |
|   | Xanthan gum | 0.2 |
|   | Gum arabic | 3 |
|   | Glycerol | 3 |
|   | Sodium dehydroacetate | 0.5 |
|   | Deionized water | 52.1 |

-continued

|   | Compounds/trade names | % by mass |
|---|---|---|
|   | Monosodium salt of n-stearoyl-L-glutamic acid, sold as Amisoft HS 11 by Ajinomoto | 1 |
| B | Deodorized organic beeswax | 14 |
|   | Organic carnauba wax | 8 |
|   | Mixture of cetylstearylglucoside and cetyl and stearyl alcohols (20/80) (sold as Montanov 68 ® by SEPPIC) | 3 |
|   | Glyceryl mono/distearate | 3 |
| C | Sorbic acid | 0.2 |
|   | 96-degree denatured absolute ethyl alcohol | 5 |
|   | TOTAL | 100 |

Phase C, composed of the mixture of sorbic acid and ethyl alcohol, is added to the mixture of phases A and B.

The composition is prepared as indicated in Example 1. Its viscosity, measured on the next day in accordance with the protocol described in Example 1, is 7.6 Pa·s.

Example 3

|   | Compounds/trade names | % by mass |
|---|---|---|
| A | Black iron oxide | 5 |
|   | Xanthan gum | 0.2 |
|   | Gum arabic | 3 |
|   | Glycerol | 3.8 |
|   | Sodium dehydroacetate | 0.5 |
|   | Deionized water | 51.3 |
|   | Monosodium salt of n-stearoyl-L-glutamic acid, sold as Amisoft HS 11 by Ajinomoto | 1 |
| B | Deodorized organic beeswax | 14 |
|   | Organic carnauba wax | 8 |
|   | Mixture of cetylstearylglucoside and cetyl and stearyl alcohols (20/80) (sold as Montanov 68 ® by SEPPIC) | 5 |
|   | Glyceryl mono/distearate | 3 |
| C | Sorbic acid | 0.2 |
|   | 96-degree denatured absolute ethyl alcohol | 5 |
|   | TOTAL | 100 |

The composition is prepared as indicated in Examples 1 and 2. Its viscosity, measured on the next day in accordance with the protocol described in Example 1, is 8.3 Pa·s.

Example 4

|   | Compounds/trade names | % by mass |
|---|---|---|
| A | Monosodium salt of n-stearoyl-L-glutamic acid, sold as Amisoft HS 11 by Ajinomoto | 0.7 |
|   | Xanthan gum | 0.6 |
|   | Gum arabic | 3 |
|   | Glycerol | 3 |
|   | Sodium dehydroacetate | 0.5 |
|   | Deionized water | 56.6 |
| B | Black iron oxide coated with aluminium stearoylglutamate (3%)[a] | 5 |
|   | Candelilla wax | 3 |
|   | Shea butter | 1 |
|   | Pure vegetable argan oil | 0.1 |
|   | Deodorized organic beeswax | 8.7 |
|   | Organic carnauba wax | 6.3 |
|   | Mixture of cetylstearylglucoside and cetyl and stearyl alcohols (20/80) (sold as Montanov 68 ® by SEPPIC) | 2.1 |

-continued

| | Compounds/trade names | % by mass |
|---|---|---|
| C | Glyceryl mono/distearate | 4.2 |
| | Sorbic acid | 0.2 |
| | 96-degree denatured absolute ethyl alcohol | 5 |
| | TOTAL | 100 |

[a]NAI-C33-7001-10 from Miyoshi

The composition is prepared as indicated in Examples 1 and 2. Its viscosity, measured on the next day in accordance with the protocol described in Example 1, is 8.5 Pa·s.

All of the compositions of Examples 1 to 4 exhibit a satisfactory charging power, allowing the eyelashes to be made up thickly.

Example 5

This example aims at demonstrating the synergy which is obtained by the simultaneous presence of a glutamic derivative and/or one of its salts and an alkylpolyglycoside.

| | A (comparative) | B (invention) | C (comparative) |
|---|---|---|---|
| Composition | 5% MONTANOV 68 ® (SEPPIC) | 4% MONTANOV 68 ® (SEPPIC) 1% Glutamate[b] | 5% Glutamate[b] |
| | 30% Phytowax olive 18L57 (SOPHIM) | 30% Phytowax olive 18L57 (SOPHIM) | 30% Phytowax olive 18L57 SOPHIM |
| | 0.6% xanthan gum | 0.6% xanthan gum | 0.6% xanthan gum |
| | 0.6% Lithium Magnesium Sodium Silicate | 0.6% Lithium Magnesium Sodium Silicate | 0.6% Lithium Magnesium Sodium Silicate |
| | QS water | QS water | QS water |
| | | Results | |
| Macroscopic aspect | Carton-pâte, not smooth | Beautiful cream, thick, waxy, glossy and smooth | Thick cream, glossy and smooth |
| Comments on microscopic observation | Very coarse dispersion of waxes | Dispersion of waxes and gels. Homogeneous dispersion | Presence of packs of gels. Heterogeneous dispersion |

[b]Amisoft HS 11 by company AJINOMOTO

This comparative test shows the advantageous effect obtained via the simultaneous presence of an acid glutamic derivative and/or one of its salts and an alkylpolyglycoside.

Thus, it is observed that said association allows the obtention of a fine and homogeneous dispersion of the wax.

The invention claimed is:

1. A mascara composition in the form of a wax-in-water emulsion, the emulsion comprising:
   at least one wax, wherein the total wax concentration, exclusive of C10-C30 fatty alcohols, is 15% to 30% by weight of the emulsion;
   monosodium N-stearoyl-L-glutamate at a concentration 0.2% to 2.0% by weight of the emulsion;
   cetylstearylglucoside at a concentration of 0.2 to 2.0% by weight of the emulsion; and
   cetylstearyl alcohol at a concentration of 1 to 10% by weight of the emulsion;
   wherein the emulsion is homogenous.

2. The mascara composition according to claim 1, wherein the monosodium N-stearoyl-L-glutamate is present in the aqueous phase of the emulsion.

3. The mascara composition according to claim 1, wherein a weight ratio of the cetylstearylglucoside to the monosodium N-stearoyl-L-glutamate is greater than or equal to 0.2.

4. The mascara composition according to claim 1, wherein a weight ratio of the cetylstearylglucoside to the monosodium N-stearoyl-L-glutamate is less than 2.0.

5. The mascara composition according to claim 1, wherein a weight ratio of the cetylstearylglucoside to the monosodium N-stearoyl-L-glutamate is greater than or equal to 0.2 and less than 2.0.

6. A method comprising applying to eyelashes the mascara composition according to claim 1.

7. A method comprising applying to eyelashes the mascara composition according to claim 2.

8. A method comprising applying to eyelashes the mascara composition according to claim 3.

9. A method comprising applying to eyelashes the mascara composition according to claim 4.

10. A method comprising applying to eyelashes the mascara composition according to claim 5.

11. A mascara composition in the form of a wax-in-water emulsion, the emulsion comprising:
    at least one wax, wherein the total wax concentration, exclusive of C10-C30 fatty alcohols, is 15% to 30% by weight of the emulsion;
    monosodium N-stearoyl-L-glutamate at a concentration 0.2% to 2.0% by weight of the emulsion;
    cetylstearylglucoside at a concentration of 0.2 to 2.0% by weight of the emulsion; and
    cetylstearyl alcohol at a concentration of 1 to 10% by weight of the emulsion; wherein:
    the emulsion is homogenous; and
    the emulsion comprises less than 1% by weight of triethanolamine and derivatives thereof.

12. The mascara composition according to claim 11, wherein the monosodium N-stearoyl-L-glutamate is present in the aqueous phase of the emulsion.

13. The mascara composition according to claim 11, wherein a weight ratio of the cetylstearylglucoside to the monosodium N-stearoyl-L-glutamate is greater than or equal to 0.2.

14. The mascara composition according to claim 11, wherein a weight ratio of the cetylstearylglucoside to the monosodium N-stearoyl-L-glutamate is less than 2.0.

15. The mascara composition according to claim 11, wherein a weight ratio of the cetylstearylglucoside to the monosodium N-stearoyl-L-glutamate is greater than or equal to 0.2 and less than 2.0.

16. A method comprising applying to eyelashes the mascara composition according to claim 11.

17. A method comprising applying to eyelashes the mascara composition according to claim 12.

18. A method comprising applying to eyelashes the mascara composition according to claim 13.

19. A method comprising applying to eyelashes the mascara composition according to claim 14.

20. A method comprising applying to eyelashes the mascara composition according to claim 15.

\* \* \* \* \*